US005922687A

United States Patent [19]
Mann et al.

[11] Patent Number: 5,922,687
[45] Date of Patent: *Jul. 13, 1999

[54] INTRACELLULAR DELIVERY OF NUCLEIC ACIDS USING PRESSURE

[75] Inventors: Michael J. Mann, Newton, Mass.; Frank P. Diet, Köln, Germany; Victor J. Dzau, Newton; Gary H. Gibbons, Lexington, both of Mass.; Heiko Von Der Leyen, Sehnde, Germany

[73] Assignee: Board of Trustees of the Leland Stanford Junior University, Palo Alto, Calif.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/745,023

[22] Filed: Nov. 7, 1996

Related U.S. Application Data

[63] Continuation-in-part of application No. 08/434,750, May 4, 1995.

[51] Int. Cl.$^6$ ..................................................... A61K 48/00
[52] U.S. Cl. ............................. 514/44; 435/440; 435/455
[58] Field of Search ................................. 435/172.3, 440, 435/455; 514/44

[56] References Cited

U.S. PATENT DOCUMENTS

| 5,328,470 | 7/1994 | Nabel et al. | 604/101 |
|---|---|---|---|
| 5,584,803 | 12/1996 | Stevens et al. | 604/4 |
| 5,698,531 | 12/1997 | Nabel et al. | 514/44 |

OTHER PUBLICATIONS

Acsadi et al., "Direct Gene Transfer and Expression into Rat Heart in Vivo", *The New Biologist*, 3:71–81 (1991).
Furth et al., "Gene Transfer into Somatic Tissues by Jet Injection", *Analytical Biochemistry*, 205:365–368 (1992).
Sindelar, "Isolation–Perfusion of the Liver with 5–Fluorouracil," *Ann. Surg.*, 201:337–343 (1985).
Skibba et al., "A Technique for Isolation Perfusion of the Canine Liver with Survival," *Journal of Surgical Research*, 34:123–132 (1983).
Wolff et al., "Expression of naked plasmids by cultured myotubes and entry of plasmids into T tubules and caveolae of mammalian skeletal muscle", *Cell Sci.*, 103:1249–1259 (1992).
Yee et al., "Cellular Uptake of Intracerebroventricularly Administered Biotin–or Digoxigenin–Labeled Antisense Oligodeoxynucleotides in the Rat", *Cellular and Molecular Neurobiology*, 14:475–486 (1994).

Nabel et al., "Recombinant Gene Expression in Vivo Within Endothelial Cells of the Arterial Wall", *Science*, 244: 1342–1344 (1989).
Nabel et al., "Site–Specific Gene Expression in Vivo by Direct Gene Transfer into the Arterial Wall", *Science* 245: 1285–1288 (1990).
Barinaga, "Step Taken Toward Improved Vectors for Gene Transfer", *Science*, 266: 1326 (1994).
Marshall, "Gene Therapy's Growing Pains", *Science*, 269: 1050–1055 (1995).
Crystal, "Transfer of Genes to Humans: Early Lessons and Obstacles to Success", *Science*, 270: 404–410 (1995).
Orkin, et al., "Report and Recommendations of the Panel to Assess the NIH Investment in Research on Gene Therapy", (1995).
Schofield, et al., "Non–viral approaches to gene therapy", *British Medical Bulletin*, 51–71 (1995).
Ledley, "Non–viral gene therapy", *Current Opinion in Biotechnology*, 5: 626–636 (1994).
Mann, Michael J. et al., *Genetic Engineering of Vein Grafts Resistant to Atherosclerosis*, Proc. National Acad. Science USA: Medical Sciences, vol. 92, pp. 4502–4506.

*Primary Examiner*—James Ketter
*Assistant Examiner*—Irem Yucel
*Attorney, Agent, or Firm*—Clark & Elbing LLP

[57] ABSTRACT

Naked nucleic acids (DNA, RNA, and/or analogs), drugs, and/or other molecules in an extracellular environment enter cells in living intact tissue upon application of pressure to the cells and extracellular environment. Nucleic acids localize to the cell nuclei. Transfection efficiencies greater than 90% are achievable for naked DNA and RNA. A sealed enclosure, defined by an enclosing means and/or tissue, contains the cells and their extracellular environment. The enclosure is pressurized to an incubation pressure on the order of atmospheres. A protective inelastic sheath may be used to prevent distension and trauma in tissue that is part of the enclosure boundary. Suitable enclosures include pressurization chambers and organs such as blood vessels or the heart. Parts of organs, entire organs, and/or entire organisms are pressurized. Suitable target tissue types include blood vessel (in particular vein) tissue, heart, kidney, liver, and bone marrow tissue. Gene therapy applications include ex-vivo treatment of grafts prior to transplantation, and in-vivo treatment of tissue. Useful therapy targets include cell cycle regulatory genes for blocking cell proliferation, and interleukin (IL) and cell adhesion molecule (CAM) genes for reducing immune responses to grafts.

90 Claims, 15 Drawing Sheets

INTRACELLULAR DELIVERY OF NUCLEIC ACIDS USING PRESSURE

This application is a continuation-in-part of U.S. patent application Ser. No. 08/434,750, filed May 4, 1995, herein incorporated by reference.

FIELD OF THE INVENTION

The present invention relates to a method for intracellular delivery of molecules such as nucleic acids, and in particular to a method using controlled pressure to effect cellular uptake of molecules.

BACKGROUND OF THE INVENTION

Efficient intracellular delivery of molecules such as drugs and/or nucleic acids (DNA, RNA and analogs) is critical for many therapies, and in particular for gene therapy. Efficient and finely localized intracellular delivery of nucleic acids is one of the most important stumbling blocks facing the practical use of gene therapy. Drug delivery methods can also benefit from an improvement in delivery efficiency and localization specificity.

Simply exposing cells to naked DNA results in relatively low transfection efficiencies. An article by Wolff et al. in *Science* 247:1465–1468 (Mar. 23, 1990), herein incorporated by reference, describes a method of direct gene transfer into mouse muscle cells. Pure DNA and RNA encoding reporter molecules (CAT or β-galactosidase) were injected directly into mouse skeletal muscle. Approximately 1.5% of the ~4000 muscle cells comprising the mouse quadriceps, and about 10–30% of the cells within the injection area were observed to display β-galactosidase activity seven days after injection of 100 μg of pRSVlac-Z DNA into individual quadriceps muscles. The method described by Wolff et al. is somewhat effective only for gene delivery to a limited injection area, and only in muscles. As indicated by Wolff et al., injection of pure DNA into other organs (liver, spleen, skin, lung, brain, and blood) results in much lower transfection efficiencies than injection in muscle. Also, the method described by Wolff et al. cannot be used to deliver DNA to large areas.

Higher transfection efficiencies can be achieved by coupling DNA to a delivery vehicle such as a liposome or a virus capsule. An article by Nabel et al. in *Science* 249:1285–1288 (Sep. 14, 1990), herein incorporated by reference, describes retroviral transfection and liposome-mediated transfection of arterial wall cells. The method allows site-specific gene transfer over a larger area than injection, but requires the use of potentially hazardous delivery vehicles. Such delivery vehicles are potentially toxic to the target cells, and can induce immunologic responses that can be harmful and/or reduce the effectiveness of gene transfer. Viral vectors are associated with risks of mutation and oncogenesis, and are not generally considered acceptable for widespread clinical applications.

OBJECTS AND ADVANTAGES OF THE INVENTION

In view of the above, it is a primary object of the present invention to provide a method for efficient, location-specific, large-area delivery of molecules, including nucleic acids, into cells of tissues. It is another object of this invention to provide an intracellular delivery method that does not cause tissue damage, and that is not potentially toxic to cells. It is yet another object of this invention to allow high-efficiency intracellular delivery of naked nucleic acids, i.e. nucleic acids free of delivery vehicles. It is yet another object to allow intracellular delivery of nucleic acids under controlled incubation pressures applied for controlled incubation periods.

It is another object of this invention to provide methods of pressurized intracellular delivery of molecules that do not cause distension and trauma in the target tissue. It is still another object to allow altering cell functions, modulating immune responses to target cells, and inhibiting cell proliferation or neoplastic growth by delivering nucleic acids under pressure. It is a further object of the invention to provide a system for delivering molecules to cells in tissue under controlled pressures.

These and other objects and advantages will become more apparent after consideration of the ensuing description and the accompanying drawings.

SUMMARY OF THE INVENTION

A nucleic acid is delivered to cells in a tissue by placing the nucleic acid in an extracellular environment of the cells, and establishing an incubation pressure around the cells and the extracellular environment. Surprisingly, the establishment of the incubation pressure facilitates the uptake of the nucleic acid by the cells, and enhances localization to the cell nuclei.

A sealed enclosure containing the tissue and the extracellular environment is defined, and the incubation pressure is established within the sealed enclosure. In a preferred embodiment, the boundary of the enclosure is defined substantially by an enclosing means, so that target tissue (tissue comprising the target cell) is subjected to isotropic pressure, and does not distend or experience trauma. In another embodiment, part of the enclosure boundary is defined by a tissue. A protective means such as an inelastic sheath is then placed around the tissue to prevent distension and trauma in the tissue.

In particular, in a blood vessel, a sealed enclosure is preferably defined between occlusions formed by inflatable balloons or tie wraps. A nucleic acid solution is delivered to the enclosure through a catheter having a delivery outlet between the occlusions. More generally, an enclosure is defined within an organ by establishing occlusions within organ conduits (e.g. blood vessels), such that a space within the organ can be pressurized.

The incubation pressure is preferably maintained at a predetermined level for a predetermined incubation period. The incubation pressure depends on the application, including parameters such as the incubation period and the tissue type. Incubation pressures between 0 and 2 atm above atmospheric (ambient) pressure are suitable for many applications. Generally, the incubation pressure is between 300 mm Hg and 1500 mm Hg above atmospheric pressure, or at least higher than 100 mm Hg above atmospheric pressure. Incubation pressures higher than 2 atm and lower than 100 mm Hg can also be used in a method of the present invention, however, depending on the application.

The incubation period necessary for achieving maximal transfection efficiency depends on parameters such as the incubation pressure and the target tissue type. For some tissue, such as human vein tissue, an incubation period on the order of minutes (>1 minute) at low pressure (~0.5 atm) is sufficient for achieving a transfection efficiency of 80–90%. For other tissue, such as rat aorta tissue, an incubation period on the order of hours (>1 hour) at high pressure (~2 atm) is necessary for achieving a transfection efficiency of 80–90%.

Suitable mammalian target tissue includes blood vessel tissue (in particular veins used as grafts in arteries), heart, bone marrow, and connective tissue, liver, genital-urinary system, bones, muscles, gastrointestinal organs, and endocrine and exocrine organs. A method of the present invention can be applied to parts of an organ, to a whole organ (e.g. heart), or to a whole organism. In one embodiment a nucleic acid solution is perfused into a target region (e.g. a kidney) of a patient, and the patient is subject to pressure in a pressurization chamber. Applications of a method of the present invention also include the treatment of allografts (grafts derived from a different subject than the transplant patient) and syngrafts (grafts derived from the transplant patient).

The nucleic acid is preferably naked, i.e. unattached to a delivery vehicle such as a liposome or a viral vector. A naked nucleic acid may be attached to other molecules such as DNA-binding proteins. In another embodiment, the nucleic acid is attached to a liposome, a viral vector, or a virus-liposome complex such as a hemagglutinating virus of Japan-(HVJ-) liposome. The nucleic acid can also be used to deliver an attached molecule of interest, such as a protein, to a cell.

Several mechanisms for the interaction between the delivered nucleic acid and the target cell are available for altering the functioning of the target cell. In one approach, the delivered nucleic acid comprises an antisense portion complementary to a target nucleic acid present in the cell. In another approach, the delivered nucleic acid is a decoy double stranded DNA chain having a binding site adapted to bind to a cellular factor. Free cellular factor binds to the binding site. Consequently the availability of the factor for normal cellular functions is reduced. In yet another approach, the nucleic acid comprises a ribozyme, i.e. a RNA chain with enzymatic activity. In still another approach the nucleic acid comprises a plasmid. If expression of the nucleic acid is desired, the nucleic acid preferably comprises a regulatory element, such as a promoter or an enhancer, operatively linked to a coding portion. The regulatory element controls the expression of the coding portion.

Applications of pressurized delivery of nucleic acids include control of cell division, inhibition of immune responses to transplant tissue, inhibition of production of deleterious proteins, and secretion of beneficial proteins. The delivered nucleic acids alter levels of target factors in the cell. Suitable targets for cell division inhibition include proteins encoded by protooncogenes, oncogenes, and/or cell cycle regulatory genes, including cyclin dependent kinase and cyclin genes. Suitable target factors for cell division inhibition include transcription factors, including E2F, NFκB, and AP1 factors. Factors affecting a body immune response to transplant cells include TGF-β, IL-10, and IL-4 (downregulators of immune responses), and IL-2 and ICAM-1 (upregulators of immune responses). For secretion of beneficial proteins, the delivered nucleic acid encodes a protein adapted to be secreted by the cell. Target proteins for secretion can be readily chosen by the skilled artisan, depending on the particular application.

More generally, a method of the present invention can be used to safely enhance the cellular uptake of a variety of molecules, including small molecules (e.g. drugs), sugars, fatty acids and derivatives, and proteins.

A system for delivering a molecule (such as a nucleic acid) into a cell comprises an enclosing means for defining at least part of a boundary of a sealed enclosure, and a pressurization means for establishing an incubation pressure within the enclosure. The enclosure contains the target cell and an extracellular environment of the cell. A delivery means such as a catheter or syringe is used to deliver the molecule to the extracellular environment, directly or indirectly (e.g. by intravenous injection).

The enclosure boundary is defined by the enclosing means, and possibly by tissue. Suitable enclosing means include, depending on the embodiment, a pressurization chamber, an impermeable sheath or bag, and occlusion means for occluding a passage in a tissue. A pressurization chamber is particularly suited for the treatment of grafts or entire organisms, while other devices are well suited for intraoperative treatment of tissue.

In one embodiment, the enclosure boundary is defined substantially by the enclosing means. Pressure is then applied to the target tissue uniformly from all directions, and the target tissue is not subjected to a risk of suffering trauma. In another embodiment, part of the boundary is defined by a tissue (e.g. the target tissue). The tissue forming part of the enclosure boundary is subjected to pressure from one side only, and can become distended. A protective means such as an inelastic sheath is placed around the tissue to prevent distension and trauma in the tissue.

DESCRIPTION OF THE FIGURES

FIG. 1-B shows the system of FIG. 1-A attached to a free end of a blood vessel, before delivery of a nucleic acid solution to the blood vessel, according to the present invention.

FIG. 1-C shows the system and blood vessel of FIG. 1-B during delivery of a nucleic acid solution to the endothelium of the blood vessel, according to the present invention.

FIG. 1-C' shows the system and blood vessel of FIG. 1-B during delivery of a nucleic acid solution to the endothelium and outside surface of the blood vessel, according to the present invention.

FIG. 3-B shows the blood vessel of FIG. 3-A, wherein the blood vessel is pressurized mechanically FIG. 4-A depicts a two-balloon catheter adapted to deliver a nucleic acid solution into a blood vessel, according to the present invention.

FIG. 4-C shows a catheter system having a balloon and inner tubules for delivering a nucleic acid solution to the walls of a blood vessel, according to the present invention.

FIG. 5-B shows the use of balloon-catheters for pressurizing an organ, according to the present invention.

FIG. 7-B illustrates the effect of a distension-preventing sheath on transfection efficiency for FITC-ODN transfected human saphenous vein, according to the present invention.

FIG. 7-C illustrates inhibition of IL-6 protein production following transfection of IL-6 antisense ODN into human saphenous vein, according to the present invention.

FIG. 8-B is a graph similar to that in FIG. 8-A, for a second subject.

FIG. 8-C is a graph similar to that in FIG. 8-A, for a third subject.

FIG. 9-B shows luciferase activity for control, healthy and atherosclerotic cells following in vivo transfection of rabbit carotid artery with DNA encoding firefly luciferase, according to the present invention.

FIG. 12-B shows ischemia-induced PCNA expression in transplanted rat aortae with and without pressure-mediated transfection of antisense-PCNA ODN, according to the present invention.

FIG. 12-C shows ischemia-induced cdc2 kinase expression in transplanted rat aortae with and without pressure-mediated transfection of antisense-cdc2 kinase ODN, according to the present invention.

FIG. 12-D shows illustrates the reduction in lumenal narrowing of isotransplanted, ischemic-injured rat aortae, resulting from pressure-mediated transfection with antisense ODN against both PCNA and cdc2 kinase, according to the present invention.

FIG. 13-B shows ICAM-1 expression in transplanted rat hearts with and without pressure-mediated transfection of antisense-ICAM-1 ODN, according to the present invention.

FIG. 13-C illustrates the induction of long-term graft acceptance by pressure-mediated transfection of transplanted rat hearts with antisense ODN against ICAM-1, according to the present invention.

FIG. 14-B shows results similar to those in FIG. 14-A for veins transfected with E2F decoy ODN, as compared to untreated grafts and control grafts transfected with scrambled ODN, according to the present invention.

DETAILED DESCRIPTION

Figure 1A:
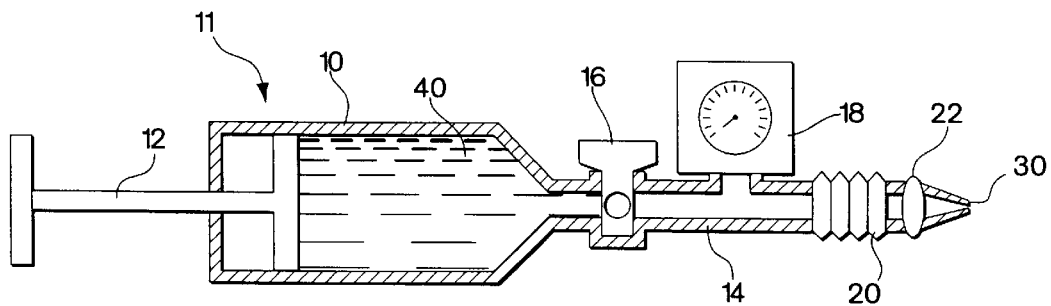
FIG. 1-A depicts a delivery system of the present invention.
Figure 1B:
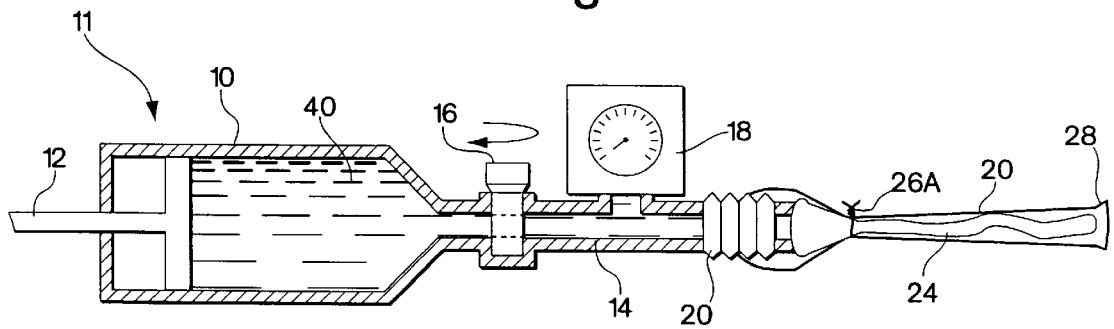
Figure 1C:
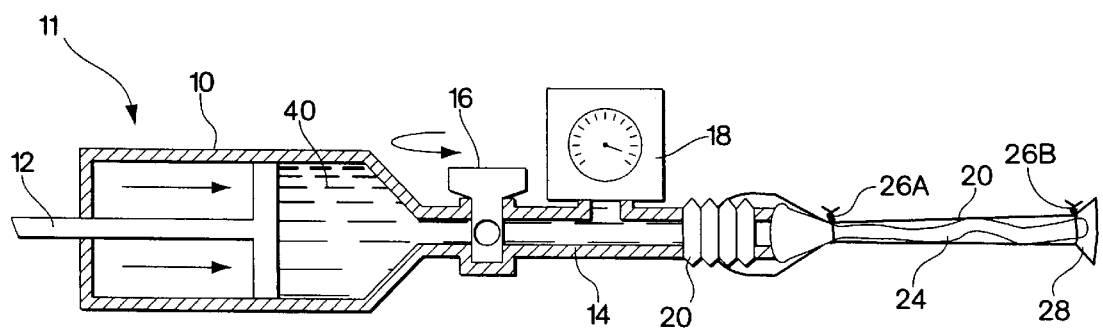
Figure 1C:
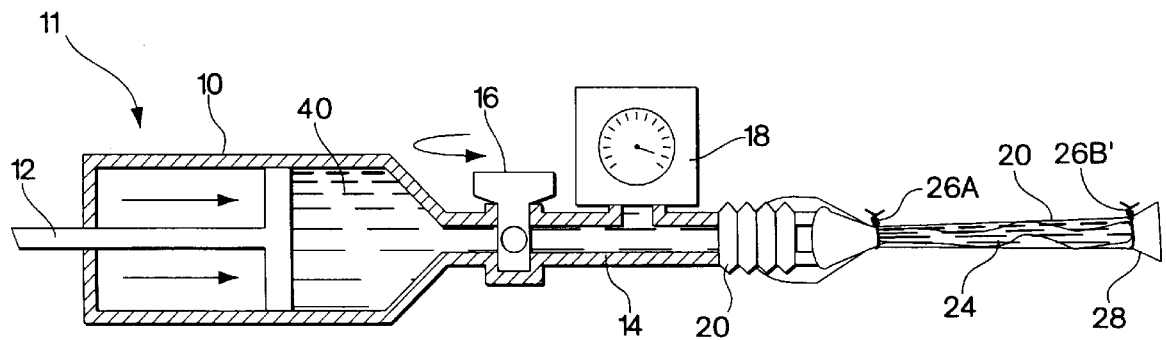

FIGS. 1-A through 1-C' illustrate methods of pressurized delivery of molecules to cells of a blood vessel. FIG. 1-A is a side view of a delivery system 11 of the present invention. System 11 comprises a reservoir 10 for holding a nucleic acid solution 40, and a delivery means for expelling solution 40 from reservoir 10. The delivery means comprises a plunger 12 and a delivery tube 14. Nucleic acid solution 40 contains DNA, RNA, nucleic acid analogs, and/or molecules attached to the DNA, RNA, and/or nucleic acid analogs. Opposite plunger 12, reservoir 10 opens into tube 14. Attached to tube 14 are, listed in order of proximity to reservoir 10, a stopcock 16, a pressure gauge 18, a retracted sheath 20, and a notch 22. Sheath 20 is preferably impermeable and inelastic. Notch 22 is next to a distal open end 30 of tube 14. Stopcock 16 is initially in a closed position, preventing solution 40 from passing from reservoir 10 to tube 14.

FIG. 1-B shows a blood vessel 24 attached to system 11. Open end 30 is placed into a proximal end of blood vessel 24. Notch 22 fits inside a proximal end of tissue 24. Sheath 20 is pulled down to cover tissue 24. A tie or ligature 26A is wrapped around sheath 20 and tissue 24 at the point where they are attached to tube 14, to prevent tissue 24 from slipping from open end 30. When stopcock 16 is turned to an open position, nucleic acid solution 40 enters tube 14 and sheath 20, flushing out all gases and liquids present through open end 28 of sheath 20. After the flushing, a tie wrap 26B is placed over distal open end 28 of sheath 20 to form a water-tight seal, as shown in FIGS. 1-C and 1-C'. FIG. 1-C illustrates delivery targeted to the endothelium of blood vessel 24, while FIG. 1-C' illustrates delivery to the endothelium and to the outside surface of blood vessel 24.

In FIG. 1-C, tie wrap 26B is placed around sheath 20 and tissue 24. Tie wrap 26B occludes blood vessel 24. Stopcock 16 is turned to its open position, and plunger 12 is pushed, such that nucleic acid solution 40 is delivered into vessel 24 under a delivery pressure. The delivery pressure is allowed to increase until an incubation pressure is reached, and stopcock 16 is closed. Blood vessel 24 is allowed to incubate for an incubation period, after which tie wrap 26B is untied to release the pressure (not illustrated).

The boundary of a sealed enclosure is defined by the walls of vessel 24 and by an enclosing means. The sealed enclosure contains the target (endothelial) cells of blood vessel 24, and their extracellular environment. If stopcock 16 is in a closed position, the enclosing means comprises tube 14, stopcock 16 and ligature 26B. If stopcock 16 is in an open position, the enclosing means comprises ligature 26B, tube 14, plunger 12 and parts of the walls of reservoir 10. The enclosing means defines at least part of the boundary of the enclosure.

In the embodiment shown in FIG. 1-C, part of the boundary of the enclosure is defined by blood vessel 24. Applying pressure only to the inside of blood vessel 24 would cause blood vessel 24 to distend, and experience trauma. Sheath 20 acts as a protective means, preventing blood vessel 24 from distending. In an arrangement such as the one in FIG. 1-C, it is thus important that sheath 20 be inelastic.

It is also possible to place tie wrap 26B around sheath 20 only, as illustrated in FIG. 1-C'. In this case, the sealed enclosure containing the target cells of blood vessel 24 and their extracellular environment is defined substantially by an enclosing means. If stopcock 16 is in a closed position, the enclosing means comprises sheath 20, tube 14, stopcock 16, and ligature 26B'. If stopcock 16 is in an open position, the enclosing means comprises sheath 20, tube 14, ligature 26B', plunger 12 and parts of the walls of reservoir 10.

In the embodiment shown in FIG. 1-C', the boundary of the enclosure is defined substantially by the enclosing means. The pressure around blood vessel 24 is uniform, and thus blood vessel 24 does not experience trauma. Since sheath 20 acts as part of the enclosing means, it is important that sheath 20 be impermeable. Sheath 20 need not necessarily be inelastic in the arrangement of FIG. 1-C', however, since the use of an elastic sheath would not lead to trauma in blood vessel 24.

Figure 2:
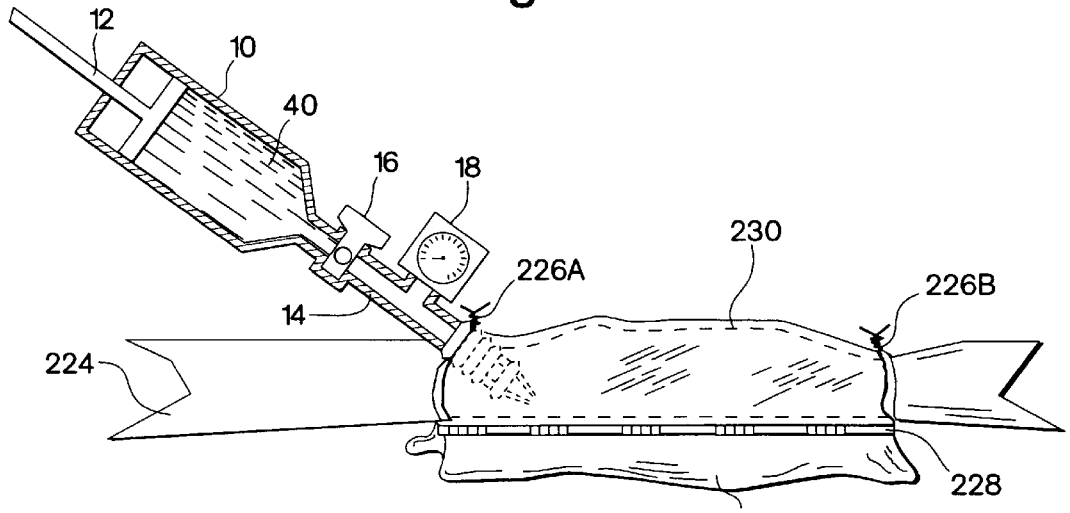
FIG. 2 illustrates delivery to a portion of a blood vessel defining part of the boundary of the pressurized enclosure, according to the present invention.

FIG. 2 illustrates a method of in vivo delivery of molecules to a blood vessel connected to the circulatory system of a patient. Tube 14 is inserted into the lumen of a vessel 224 which is still connected to the body of a living animal. A sheath 220 wraps around vessel 224, and a fastener 228 (e.g. a heat seal) attaches the two flaps of sheet 220 to form a tube. Sheath 220 acts as a protective means, preventing the distension of vessel 224. Two tie wraps 226A and 226B wrap around sheath 220. Tie wraps 226A and 226B act as occluding means, occluding vessel 224. Occlusions 226A and 226B, and the walls of vessel 224 between occlusions 226A and 226B define a sealed enclosure 230 containing the target cells of vessel 224 and their extracellular environment. Nucleic acid solution 40 is injected into the sealed enclosure, and segment 230 is allowed to incubate for an incubation period. After the incubation period occlusions 226A and 226B are removed, and blood is allowed to flow through vessel 224.

Figure 3A:
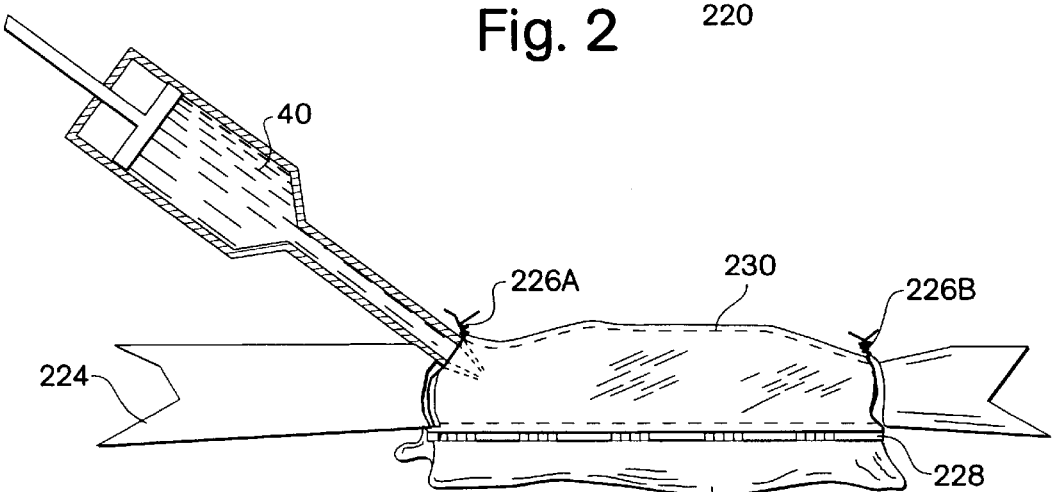
FIG. 3-A depicts an alternative method of intracellular delivery to a blood vessel, according to the present invention.
Figure 3B:
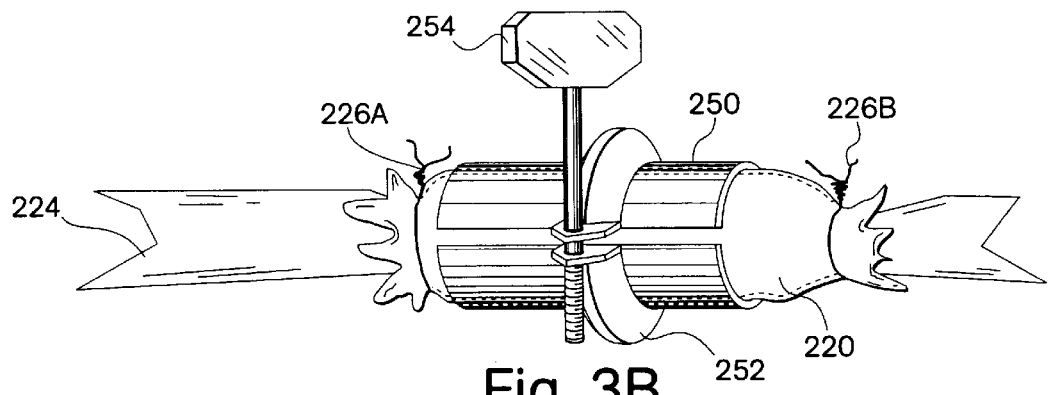

FIGS. 3-A and 3-B illustrate a delivery system having distinct delivery and pressurization elements, used to deliver molecules to the blood vessel shown in FIG. 2. A rigid tubular wrap 250 is placed around sheet 220, and a vise 252 is placed around wrap 250, as illustrated in FIG. 3-B. Wrap 250 is circumferentially flexible, so that the diameter of the tube it forms is variable, but it is rigid axially, so that even when its diameter changes, it still remains substantially tubular. A tightening screw 254 tightens vise 252, pulling wrap 250 tight, creating pressure within vessel 224. This pressure is maintained for an incubation period, after which screw 254 is unscrewed.

Figure 4A:
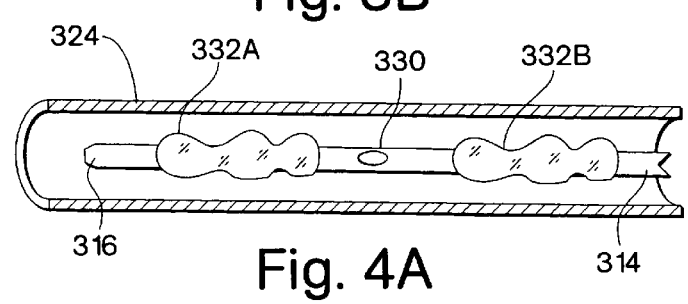
FIG. 4-B shows the catheter of FIG. 4-A with the balloons in an inflated state, according to the present invention.
Figure 4B:
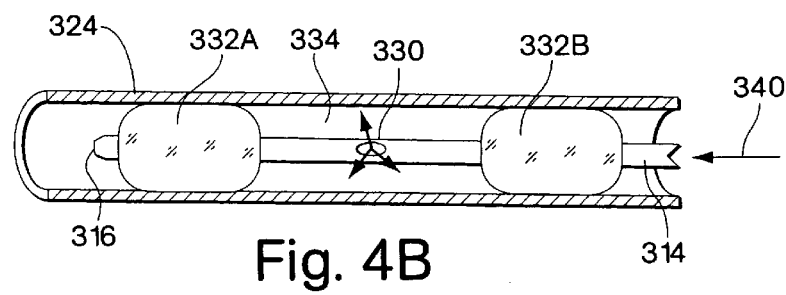
Figure 4C:
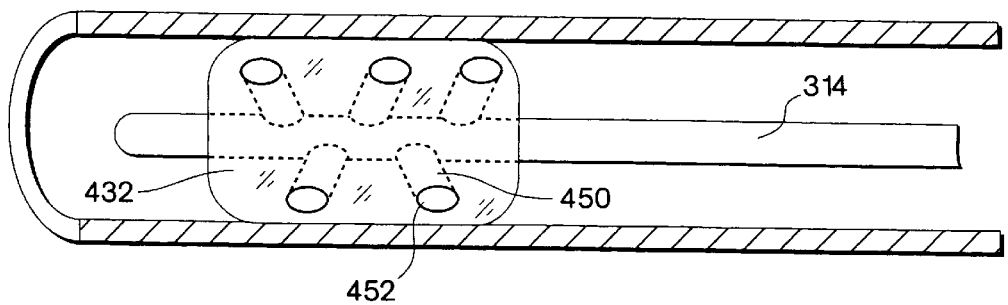

FIGS. 4-A through 4-D illustrate a method of delivering a nucleic acid solution to the lumen of a blood vessel 324 through a catheter 314. Catheter 314 is inserted into vessel 324. Catheter 314 is closed at its end 316. Catheter 314 has two balloons 332A and 332B, and a delivery port 330 between balloons 332A and 332B. Initially, balloons 332A and 332B are deflated, as shown in FIG. 4-A. After catheter 314 is inserted into vessel 324, balloons 332A and 332B are inflated, as shown in FIG. 3-B. Balloons 332A and 332B occlude vessel 324 and create a sealed enclosure 334 within vessel 324. A nucleic acid solution 340 is delivered to enclosure 334 through port 330. Solution 340 is delivered under pressure, such that enclosure 334 becomes pressurized. Following an incubation period, balloons 332A and 332B are deflated and target enclosure 334 is depressurized.

FIG. 4-C shows an alternative delivery system of the present invention, in which a balloon mounted on a catheter has miniature tubules for delivering the nucleic acid solution to the walls of the vessel. A balloon 432 has tubules 450 which are directly connected to holes 452 in the segment of catheter 314 within balloon 432. When a pressurized nucleic acid solution 440 is delivered through catheter 314, solution 440 exits holes 452, travels through tubules 450, and reaches the walls of vessel 324.

Figure 5A:
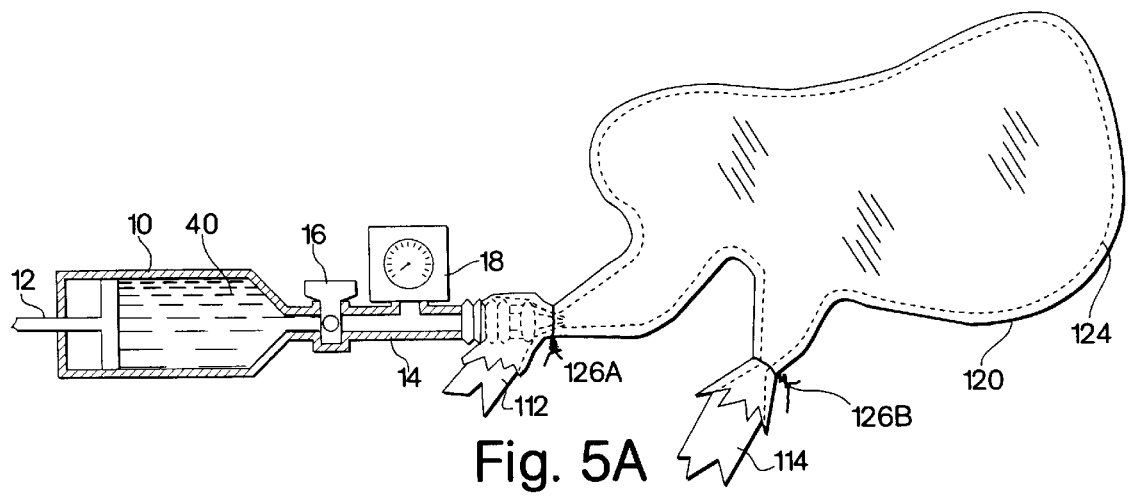
FIG. 5-A illustrates delivery to blood vessels in an organ, according to the present invention.
Figure 5B:
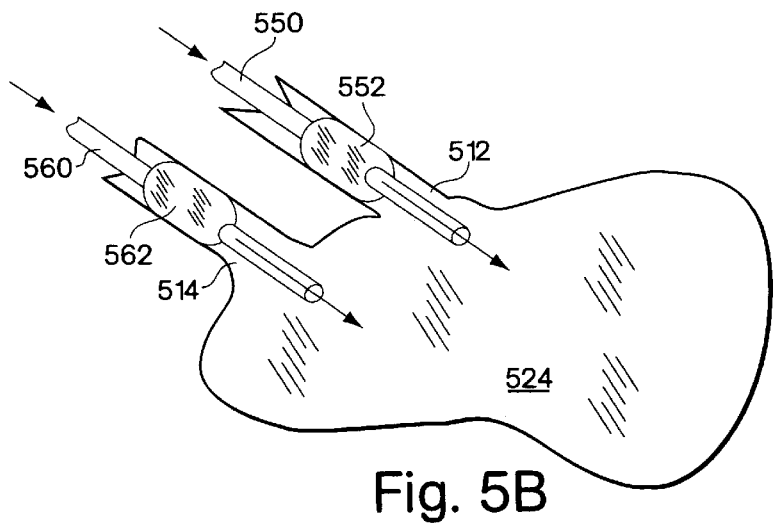

FIG. 5-A illustrates the use of system 11 for delivery to blood conduits (vessels and/or atria and ventricles) of an organ 124 such as a heart. A protective sheath 120 is wrapped around organ 124. Organ 124 has an artery 112 which carries blood into it and a vein 114 which carries blood away. Tube 14 is inserted into the lumen of artery 112, and sheath 120 is wrapped around artery 112 and vein 114. Tie wrap 126A is tightened around sheath 120 at artery 112, and tie wrap 126B is tightened around sheath 120 at vein 114, to prevent leakage of fluid out of organ 124. Tie wrap 126A allows tube 14 to enter artery 112, yet wraps tightly enough to seal artery 112 from leakage. Nucleic acid solution 40 is injected, and organ 124 is allowed to incubate. After the incubation period, tie wraps 126A and 126B are removed, and blood is allowed to flow through organ 124 once more.

FIG. 5-B illustrate the use of balloon-catheters for sealing an inlet and an outlet of an organ (e.g. a gastrointestinal organ). A catheter 550 with a balloon 552 is inserted into a first organ conduit 512 in communication with an organ 524, and another catheter 560 with a balloon 562 is inserted into a second organ conduit 514 leading away from organ 524. Initially balloons 552 and 562 are deflated (not illustrated). Once catheters 550, 560 are inserted into their respective blood vessels, balloons 552, 562 are inflated and establish occlusions in conduits 512, 514, respectively. A nucleic acid solution 540 is delivered to organ 524 under a delivery pressure.

Figure 6:
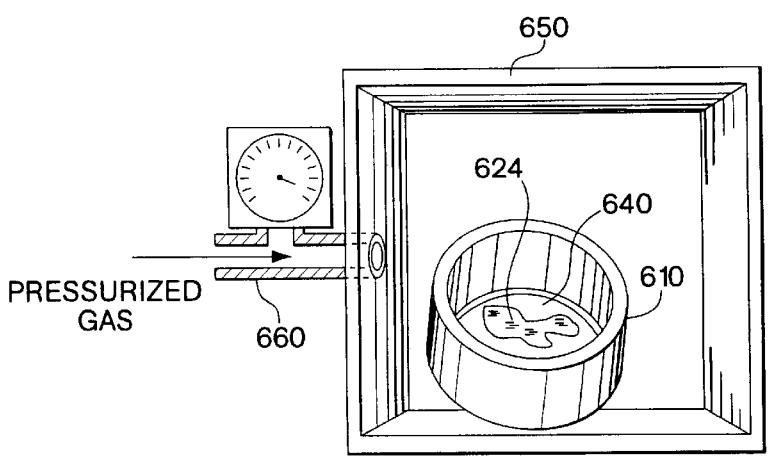
FIG. 6 shows a delivery system comprising a pressurization chamber, according to the present invention.

FIG. 6 illustrates the use of a pressurization chamber to facilitate delivery of nucleic acids to cells. A holding means such as a dish 610 contains a tissue 624 comprising target cells. A nucleic acid solution 640 is placed in dish 610. Dish 610 is placed in a pressure chamber 650. Chamber 650 is closed and sealed, and a pressurized gas (e.g. $CO_2$) is introduced into chamber 650 through a duct 660. Solution 640 and tissue 624 are maintained under an incubation pressure for an incubation period. Tissue 624 can comprise an entire organ.

A pressurization chamber such as the one shown in FIG. 6 is particularly suited to a delivery method in which an entire organism is pressurized. In such a method, a nucleotide solution is preferably perfused into blood vessels and/or organs (e.g. kidney) of a patient. The patient is placed in the pressurization chamber. The pressurization chamber is then maintained under an incubation pressure, for an incubation period.

Generally, a method of the present invention is suitable for intracellular delivery of nucleic acids in a variety of tissue types. Suitable tissue types include cardiovascular, gastrointestinal, liver, kidney, bone marrow, bone, muscle, endocrine, and exocrine tissue. The exact delivery parameters (incubation pressures, periods, temperatures, etc.) can be readily determined by the skilled artisan for a given tissue type, and for given transfection efficiency requirements.

Preferably, nucleic acids delivered according to a method of the present invention are naked, i.e. unassociated with a delivery vehicle such as a liposome or a viral vector. Such delivery vehicles, in particular viral vectors, are known to cause adverse immune responses in patients. A method of the present invention can be used, however, in conjunction with delivery vehicles. In one embodiment, the nucleic acid is attached to a liposome. In an alternative embodiment, the nucleic acid is attached to a viral vector. Lipofection and viral transfection are well known in the art, and will not be discussed here in detail. In another embodiment, the nucleic acid is attached to a virus-liposome complex such as a HVJ-(hemagglutinating virus of Japan-) liposome. For a description of HVJ-liposomes, see for example the article by Morishita et al. in *Proc. Acad. Nat. Sci. USA* 90:8474–8478 (1993), herein incorporated by reference.

As is apparent to the skilled artisan, the type (DNA or RNA, double stranded or single stranded) and sequence of a nucleic acid delivered by a method of the present invention are chosen according to the application, and the desired mechanism of interaction with the target cell. A method of the present invention has many potential applications, including control of cell division, inhibition of immune responses to transplant tissue, and secretion of beneficial proteins. Also, several mechanisms for interaction between the delivered nucleic acid and the target cell are available for altering the functioning of the target cell. Such mechanisms involve interactions of the delivered nucleic acid with target nucleic acids and/or target proteins within the cell, expression of the delivered nucleic acid, and/or catalysis of a reaction by the nucleic acid (ribozyme).

In one approach, the delivered nucleic acid comprises an antisense portion complementary to a target nucleic acid present in the cell. The sequence of the antisense portion is complementary to a target sequence, which comprises a recognizable part of a target gene. The single-stranded, DNA or RNA, antisense nucleic acid binds to RNA and/or DNA of the target gene, and inhibits its expression.

For cell division inhibition, useful antisense targets include recognizable parts of protooncogenes, oncogenes, and cell cycle regulatory genes. Useful cell cycle regulatory targets include cdk (cyclin-dependent kinases), and cyclin genes. In a preferred embodiment, the delivered nucleic acids comprise DNA chains antisense to cdc2 kinase and to proliferating cell nuclear antigen (PCNA). Other suitable target genes for cell division inhibition are well known in the art.

For inhibition of an immune response of a transplant patient to a cell in a graft, useful antisense targets within the cell include genes encoding factors recognized by immune cells, or any proteins which mediate an immune response. Such targets include genes encoding interleukin-2 (IL-2) and intercellular adhesion molecule-1 (ICAM-1). Other suitable targets for immune response suppression are known in the art.

In another mechanism of interaction with the target cell, the delivered nucleic acid comprises a decoy double-stranded DNA chain having a binding site. The sequence of the binding site is chosen such that a target cellular factor present in the cell is adapted to bind to the binding site. The binding of the cellular factor to the decoy binding site reduces the availability of the cellular factor for its normal cellular function. Suitable target factors for cell division inhibition include the transcription factors E2F, NFκB (nuclear transcription factor kappa.B), and AP1.

In yet another approach to interacting with the target cell, the delivered nucleic acid comprises a coding portion operatively linked to a regulatory element such as a promoter or enhancer. The regulatory element controls the expression of the coding portion. For inhibition of an immune response to the target cell, suitable factors encoded by the coding portion include transforming growth factor β (TGF-β), interleukin 10 (IL-10), and interleukin 4 (IL-4). For inducing the target cell to secrete a desired protein, the coding portion preferably comprises a section encoding a N-terminus signal sequence for exocytosis, as well as a section encoding the desired protein.

A particularly useful application of the present invention comprises the genetic treatment of vascular grafts. As explained in detail in the article by Mann et al. In *Proc. Acad. Nat. Sci. USA* 92:4502–4506 (1995), herein incorporated by reference, vascular grafts are prone to atherosclerosis and occlusion that ultimately lead to graft failure. Vein grafts transplanted into arteries are particularly susceptible to accelerated atherosclerosis. Vein grafts are subject to ischemic injury at the time of surgery, and to injury due to the high pressures and shear stresses in an arterial environment. Such injuries promote neointima formation in vein grafts. The neointimal hyperplasia reduces the high-distensibilities of the veins and thus helps the vein grafts adapt to the arterial environment, but can lead to graft failure. Up to 50% of vein bypass grafts fail within 10 years as a result of the proliferation of neointimal smooth muscle cells.

Inhibition of neointimal hyperplasia leads to medial hypertrophy in the vein grafts. Medial hypertrophy adds mechanical stability to the grafts without hindering blood flow. Inhibition of neointimal hyperplasia is preferably achieved by reducing an intracellular concentration of cell-cycle-regulatory factors, and/or of transcription factors. Blocking the expression of genes encoding cdc2 kinase and PCNA has been shown to prevent neointimal hyperplasia following arterial balloon injury, as explained in detail in the above-incorporated article by Morishita et al. In *Proc. Acad. Nat. Sci. USA* 90:8474–8478 (1993). In one embodiment of the present invention, antisense DNA to cdc2 kinase and to PCNA is delivered under pressure to a vein endothelium. Examples of suitable antisense sequences can be found in the above-incorporated article by Mann et al. In *Proc. Acad. Nat. Sci. USA* 92:4502–4506 (1995).

The following discussion and examples are intended to illustrate the invention, and should not be construed to limit the scope of the invention.

Discussion and Examples

There are several possible mechanisms underlying the increased permeability to nucleic acids and other molecules of cell membranes under pressure. The increase in membrane permeability requires an increased pressure within the cell and/or extracellular environment, but not ncessarily a pressure gradient across the cell membrane. It is possible that proteins forming transmembrane channels change conformation at high pressure, and thus allow the passage of nucleic acids and other molecules through the channels and into the cytoplasm. Nucleic acids then enter the cell nuclei through the cytoplasm.

The exact pressures, incubation periods and concentrations used depend on the target tissue type. For example, an incubation period of approximately 5 minutes at low pressure (~0.5 atm) is sufficient for achieving a near-maximal transfection efficiency in human saphenous vein, while an incubation period of over one hour at high pressure (~2 atm) is required for achieving a transfection efficiency of 80–90% in rat aortae. For rat hearts, an incubation period of 30 to 45 minutes at 2 atm is necessary for a transfection efficiency above 50%. In general, the incubation period necessary to achieve a given transfection efficiency in different tissue types varies from minutes to hours, at incubation pressures on the order of atmospheres. Suitable incubation periods and pressures for a given tissue type can be readily determined by the skilled artisan.

In the absence of limitations imposed by surgical procedures, it is in general preferred that the walls of the pressurized enclosure do not include living tissue, since tissue forming parts of the enclosure wall is subject to mechanical stress. Some surgical procedures, such as the treatment of blood vessels connected to the circulatory system during the procedure (see FIGS. 3-A and 3-B), require that at least parts of the enclosure walls be defined by tissue. In such a case, it is important that a protective means be used to prevent distension of the tissue. Grafts treated ex-vivo are, in general, preferably treated by incubation in a pressurized chamber or an equivalent pressurized enclosure.

Transfection efficiencies of methods of the present invention were evaluated for various incubation pressures, incubation periods, and tissue types. Some of the abbreviations used in the following discussion are: CTRL, control; ELISA, enzyme-linked immunosorbent assay; FITC, fluorescein isothiocyanate; FITC-ODN, FITC-labeled oligodeoxyribonucleotide; IL-6, interleukin-6; ODN, oligodeoxyribonucleotide; PCR, polymerase chain reaction; VSMC, vascular smooth muscle cell. The number n refers to the number of subjects evaluated for each data point. The pressures given are the net pressures applied to the samples, above ambient (atmospheric) pressure.

EXAMPLE 1

Figure 7A:
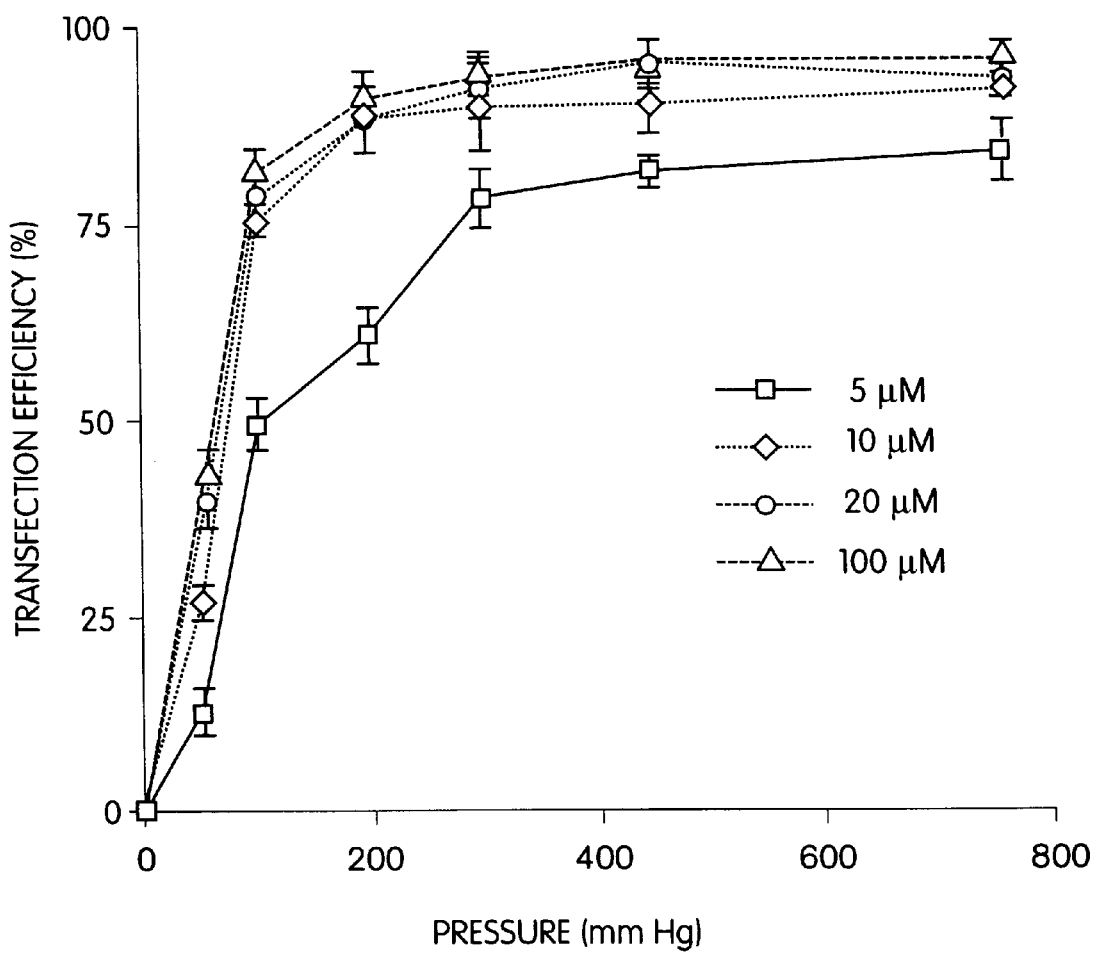
FIG. 7-A shows transfection efficiency as a function of applied pressure for human saphenous vein transfected according to the present invention.
Figure 7B:
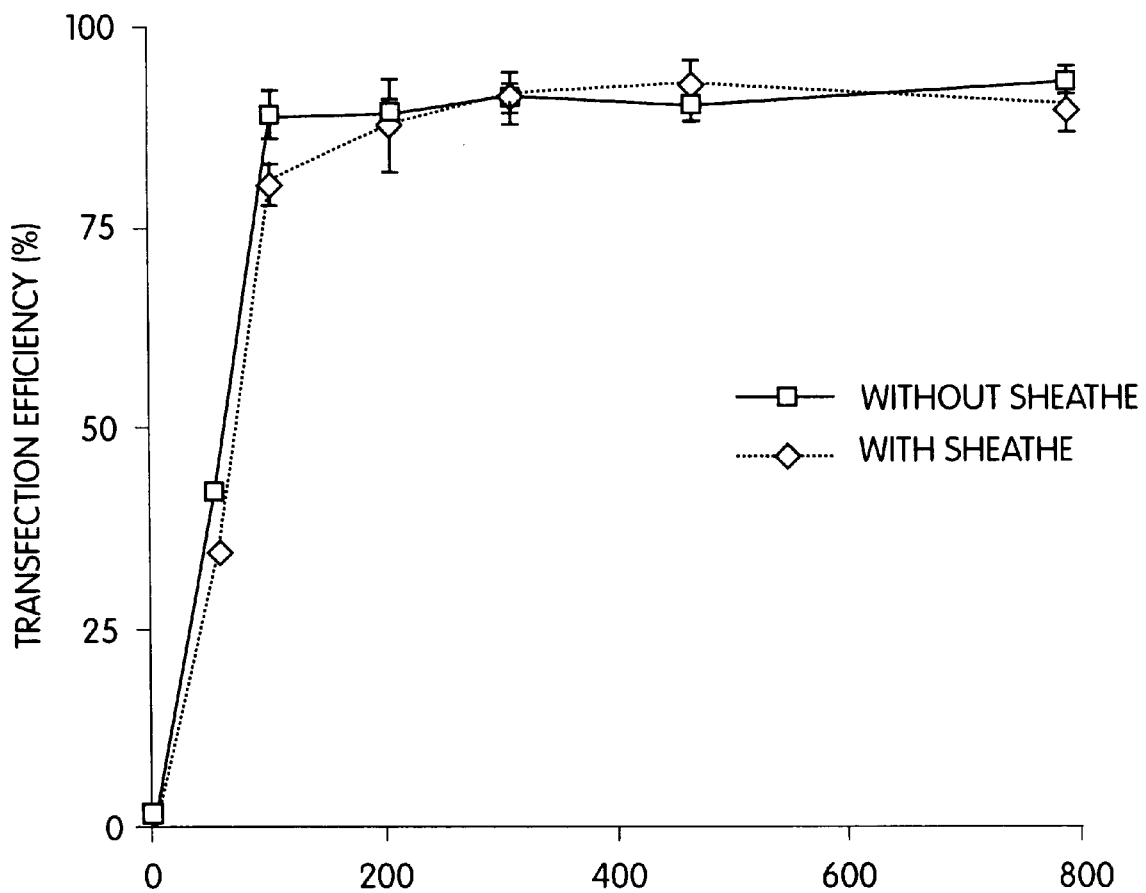
Figure 7C:
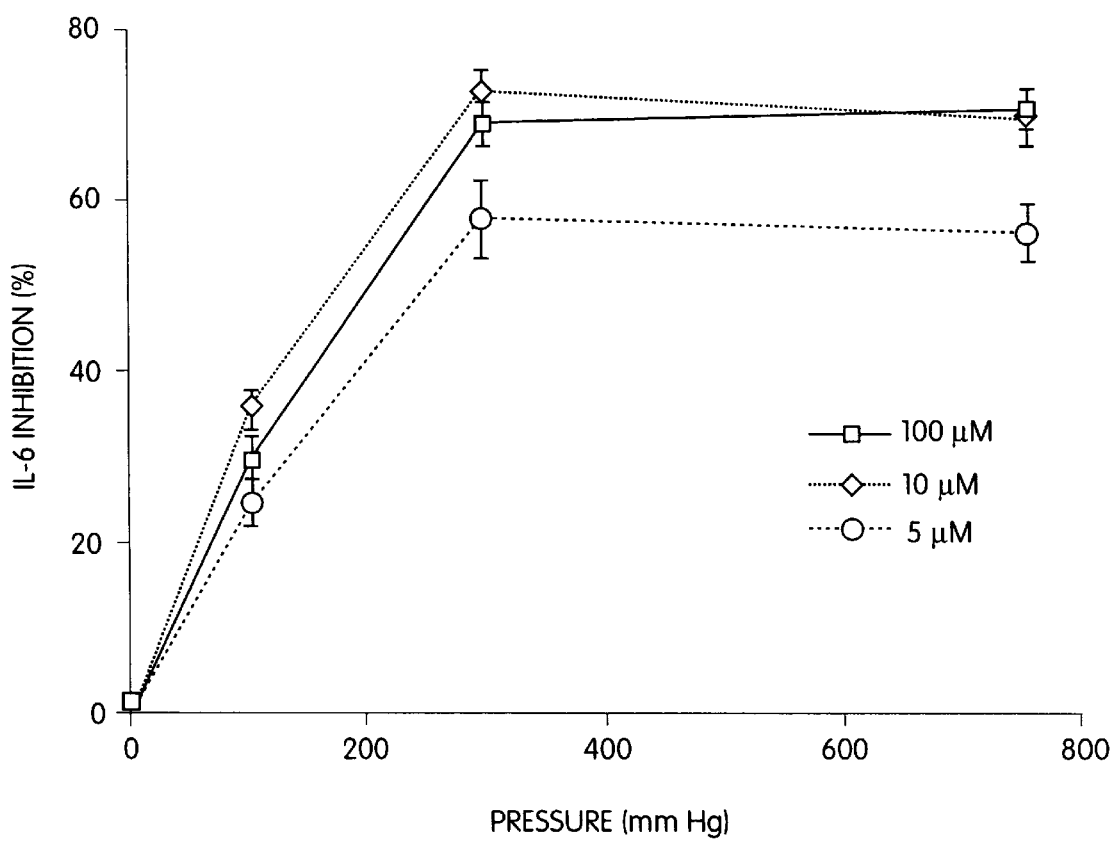

Human saphenous vein was transfected with FITC-ODN, according to a method similar to that illustrated in FIG. 1-C. FIG. 7-A shows transfection efficiency as a function of applied pressure, for several ODN concentrations. Efficiency was measured as percentage of total intimal and medial cells found to have nuclear localization of FITC-ODN via fluorescence microscopy. Pressures ranged from 50 to 760 mm Hg, and ODN concentrations in physiologic saline solution ranged from 5 to 100 $\mu$M. n=6.

The effect of a distension-preventing sheath on transfection efficiency was evaluated using a method similar to that illustrated in FIG. 1-C, at an ODN concentration of 20 $\mu$M and at pressures ranging from 50 to 760 mm Hg. FIG. 7-B shows the results of the experiment. n=6.

The transfection efficiency of a method of the present invention was investigated in vitro by measuring the inhibition of IL-6 production by antisense ODN in whole organ culture. Vein segments were incubated in growth medium for 24 hours after transfection. Tranfections were performed at 5 $\mu$M, 10 $\mu$M and 100 $\mu$M for 10 minutes, according to a method similar to that illustrated in FIG. 1-C. FIG. 7-C shows reductions in IL-6 protein detected via ELISA in growth medium for antisense-transfected cultures. The reduction levels shown are relative to the levels found in control cultures of untransfected and non-specific ODN-transfected veins. n=6.

EXAMPLE 2

Figure 8A:
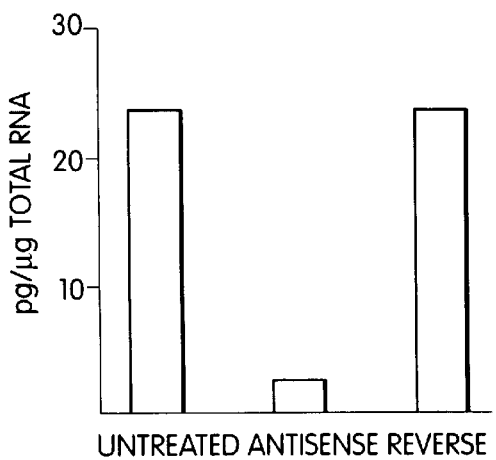
FIG. 8-A Illustrates inhibition of IL-6 mRNA production following transfection of IL-6 antisense ODN into human saphenous vein of a first subject, according to the present invention.
Figure 8B:
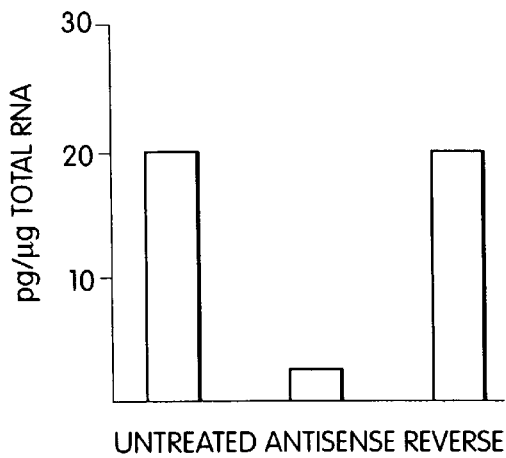
Figure 8C:
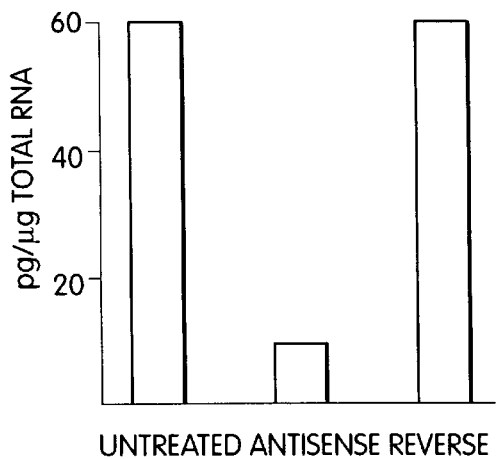

Quantitative reverse transcription PCR was used to measure the reduction in IL-6 mRNA resulting from antisense-ODN transfection performed according to the present invention. Three specimens of human saphenous vein were transfected as illustrated in FIG. 1-C, and mRNA levels in antisense-transfected vein segments were compared to levels in untreated and reverse antisense (control) ODN-transfected segments. Results for the three specimens are shown in FIG. 8-A, 8-B and 8-C, respectively. Reductions in mRNA levels indicate sequence-specific efficacy of antisense-ODN treatment.

EXAMPLE 3

Figure 9A:
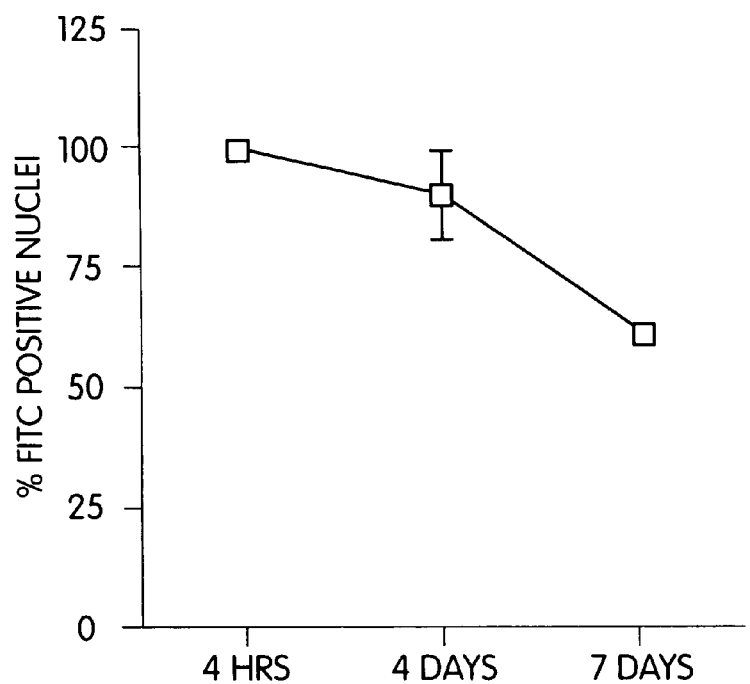
FIG. 9-A shows transfection efficiency for in vivo transfection of rabbit carotid artery measured by fluorescence microscopy, according to the present invention.
Figure 9B:
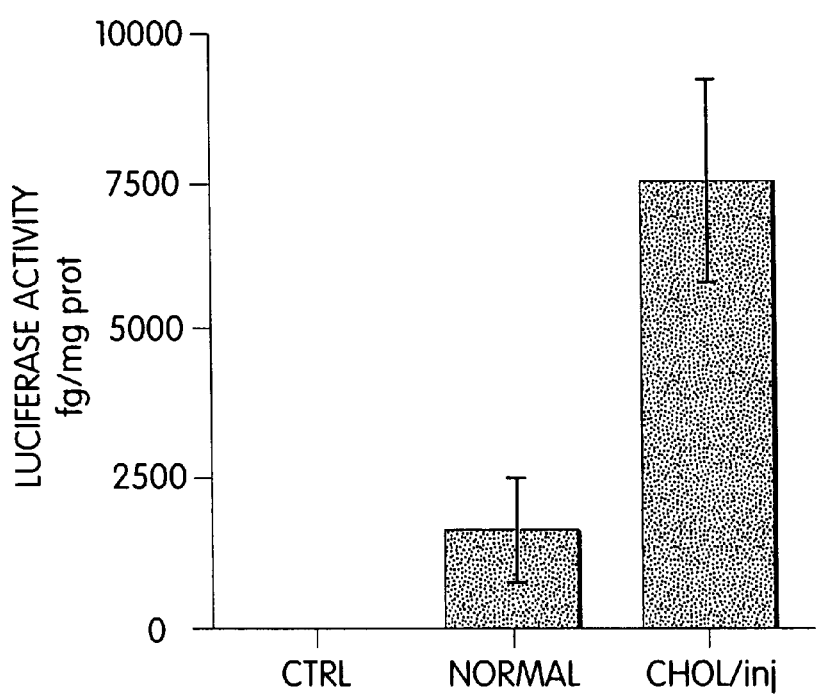

Rabbit carotid arteries were transfected in vivo with FITC-ODN, according to a method similar to that illustrated in FIG. 2. Transfection efficiency was measured at 4 hours, 4 days, and 7 days after transfection. The percentages of FITC-positive nuclei as a function of time are shown in FIG. 9-A. n=2-3.

Expression of the gene for firefly luciferase was measured after in vivo transfection of rabbit carotid artery with a plasmid DNA construct containing the luciferase gene. Healthy arteries (Normal) and atherosclerotic vessels (CHOL/inj) were transfected under pressure, as shown in FIG. 2. Control (CTRL) artery was exposed to the plasmid carrying the luciferase gene in the absence of pressure. Arteries were harvested at day 5 and tissue homogenates were assayed for luciferase activity. Assay results are shown in FIG. 9-B. n=2-4.

EXAMPLE 4

Figure 10:
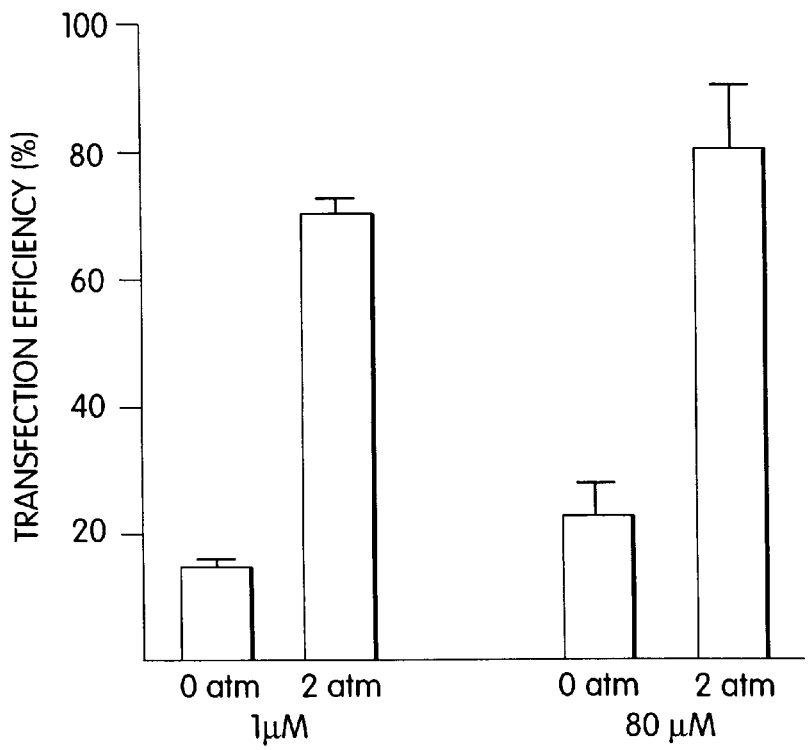
FIG. 10 shows transfection efficiencies for rat vascular smooth muscle cells transfected in vitro according to a method of the present invention.

Rat vascular smooth muscle cells (VSMC) were transfected in vitro with FITC-ODN, as shown in FIG. 6. Cells were exposed to either atmospheric pressure (0 atm net pressure) or to 2 atm for 45 minutes. FIG. 10 shows transfection efficiencies for FITC-ODN concentrations of 1 $\mu$M and 80 $\mu$M. n=4.

EXAMPLE 5

Figure 11:
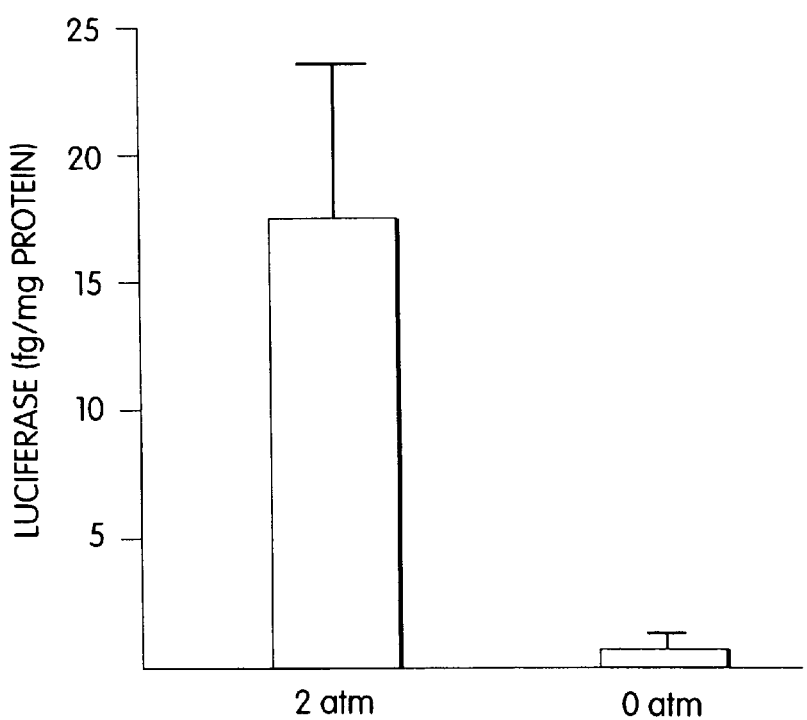
FIG. 11 shows luciferase activities for rat kidneys perfused with plasmid DNA containing the gene encoding firefly luciferase, according to the present invention.
Figure 12A:
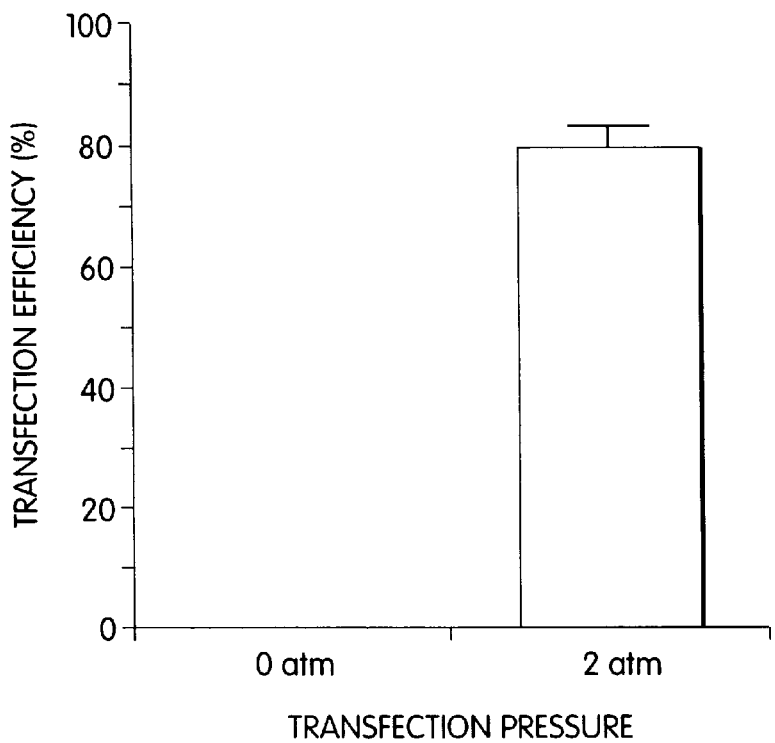
FIG. 12-A shows shows the effect of pressure on transfection efficiency for rat aorta cells, according to the present invention.
Figure 12B:
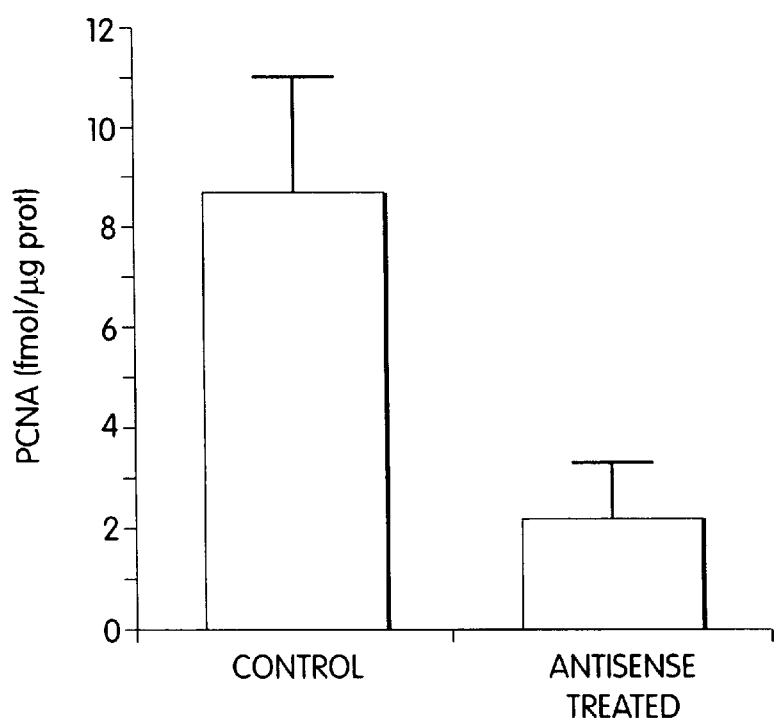
Figure 12C:
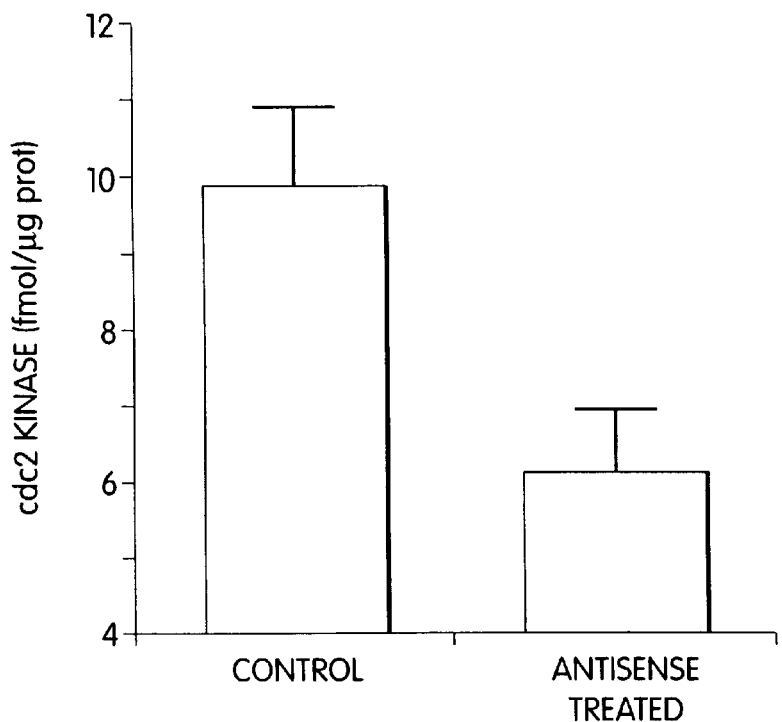
Figure 12D:
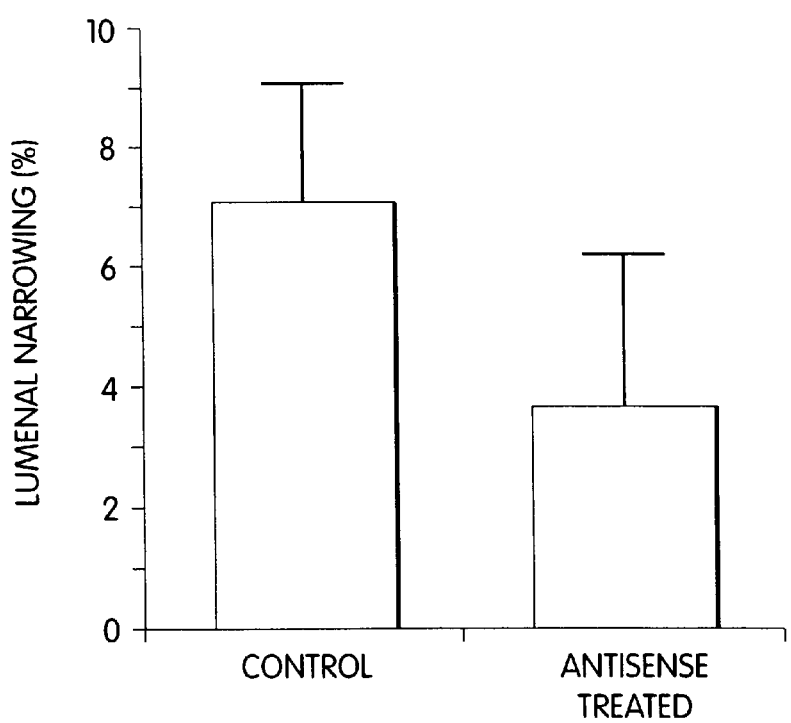

FIG. 11 illustrates the effect of pressure on transfection efficiency for rat kidney cells perfused in vivo with plasmid DNA containing the gene for firefly luciferase, as illustrated in FIG. 6. Rats were exposed to atmospheric pressure (0 atm) or 2 atm for 30 minutes after kidney perfusion. Kidneys were harvested 3 days after transfection and tissue homogenates were assayed for luciferase activity. n=7.

EXAMPLE 6

FIG. 12-A shows the effect of pressure on transfection efficiency for rat aorta cells. Aortae were harvested from donor rats and incubated at 4° C. for 24 hours in physiologic solution to induce ischemic injury, in a manner similar to that illustrated in FIG. 1-C'. The incubation solutions contained 40 $\mu$m FITC-ODN. Incubations were performed at 0 atm and 2 atm above atmospheric pressure. Following incubation, the tissue was isotransplanted into rat aortae and harvested 24 hours after transplantation. Nuclear localization of FITC was assessed by fluorescence microscopy of sections co-stained with a fluorescent DNA-intercalating dye. Transfection efficiency is expressed as cells displaying nuclear localization of FITC-ODN as a percent of total cells. n=3, p<0.005.

FIG. 12-B shows ischemia-induced PCNA expression in transplanted rat aortae with and without pressure-mediated transfection of antisense-PCNA ODN. The transfection procedure was similar to that illustrated in FIG. 1-C'. Ischemic injuries were induced by 24 hr. incubations at 4° C., either in saline solution (control), or in saline solution containing 40 $\mu$M ODN. A pressure of 2 atm above atmohsperic pressure was applied during incubation to both control and ODN-treated samples. Tissue was harvested six days after isotransplantation, and PCNA protein levels in tissue homogenates were measured by ELISA. n=7, p=0.02.

FIG. 12-C shows ischemia-induced cdc2 kinase expression in transplanted rat aortae with and without pressure-mediated transfection of antisense-cdc2 kinase ODN. The transfection, transplantation, and harvesting procedures were similar to those described above in relation to FIG. 12-B. Protein levels for cdc2 kinase were measured by ELISA.

FIG. 12-D illustrates the reduction in lumenal narrowing of isotransplanted, ischemic-injured rat aortae, resulting from pressure-mediated transfection with antisense ODN against both PCNA and cdc2 kinase. Ischemic injury was induced by 24 hrs. of incubation at 4° C. In either saline solution (control), or antisense-PCNA/antisense-cdc2 kinase ODN solution (40 µM each). A pressure of 2 atm above ambient pressure was applied to all tissues (including control). Blockade of expression of the two cell cycle regulatory genes reduced neointimal hyperplasia and lumenal narrowing in ischemically injured isografts, as measured by computerized image analysis. n=12, p=0.03.

EXAMPLE 7

Figure 13A:
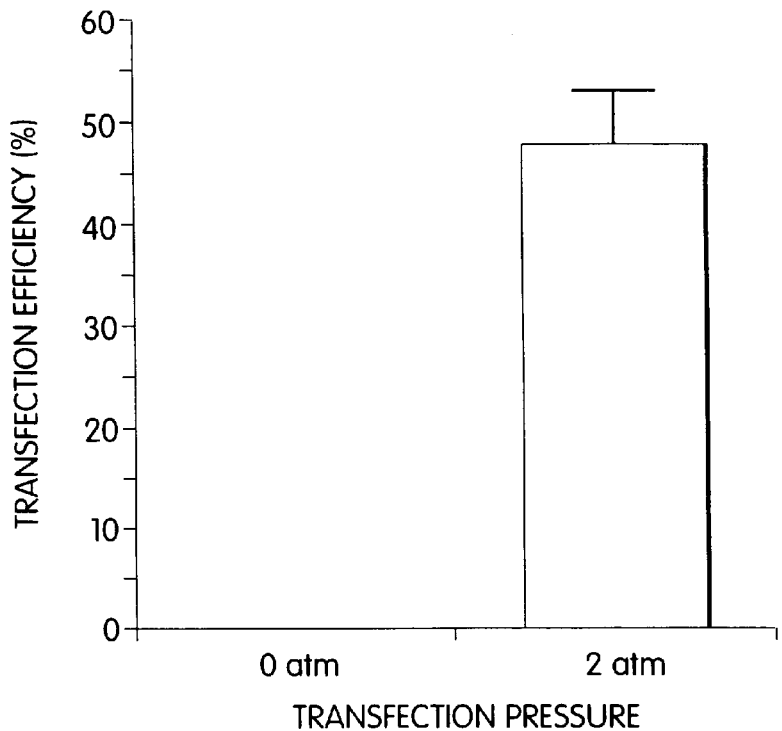
FIG. 13-A shows transfection efficiencies for rat hearts transfected ex vivo with FITC-ODN, with and without pressure, according to the present invention.
Figure 13B:
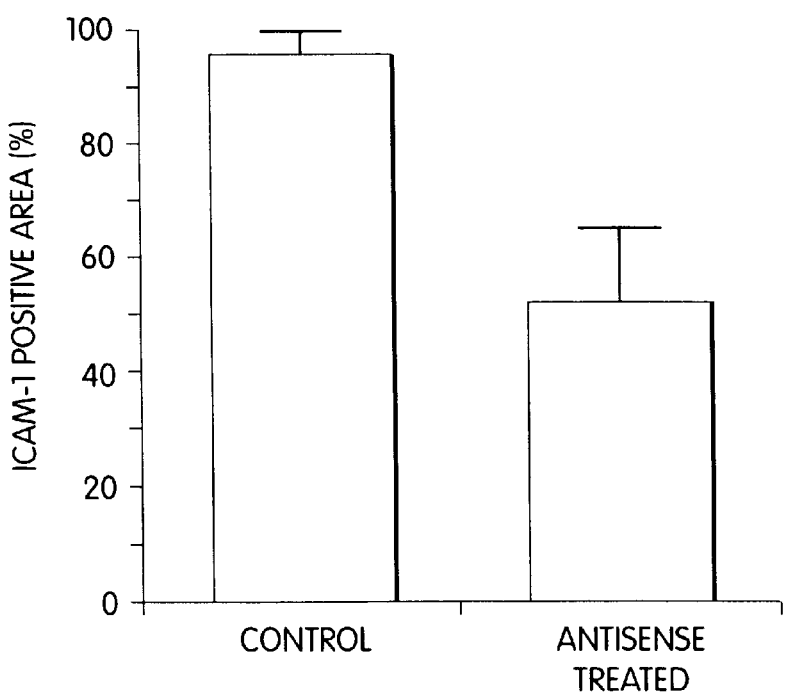
Figure 13C:
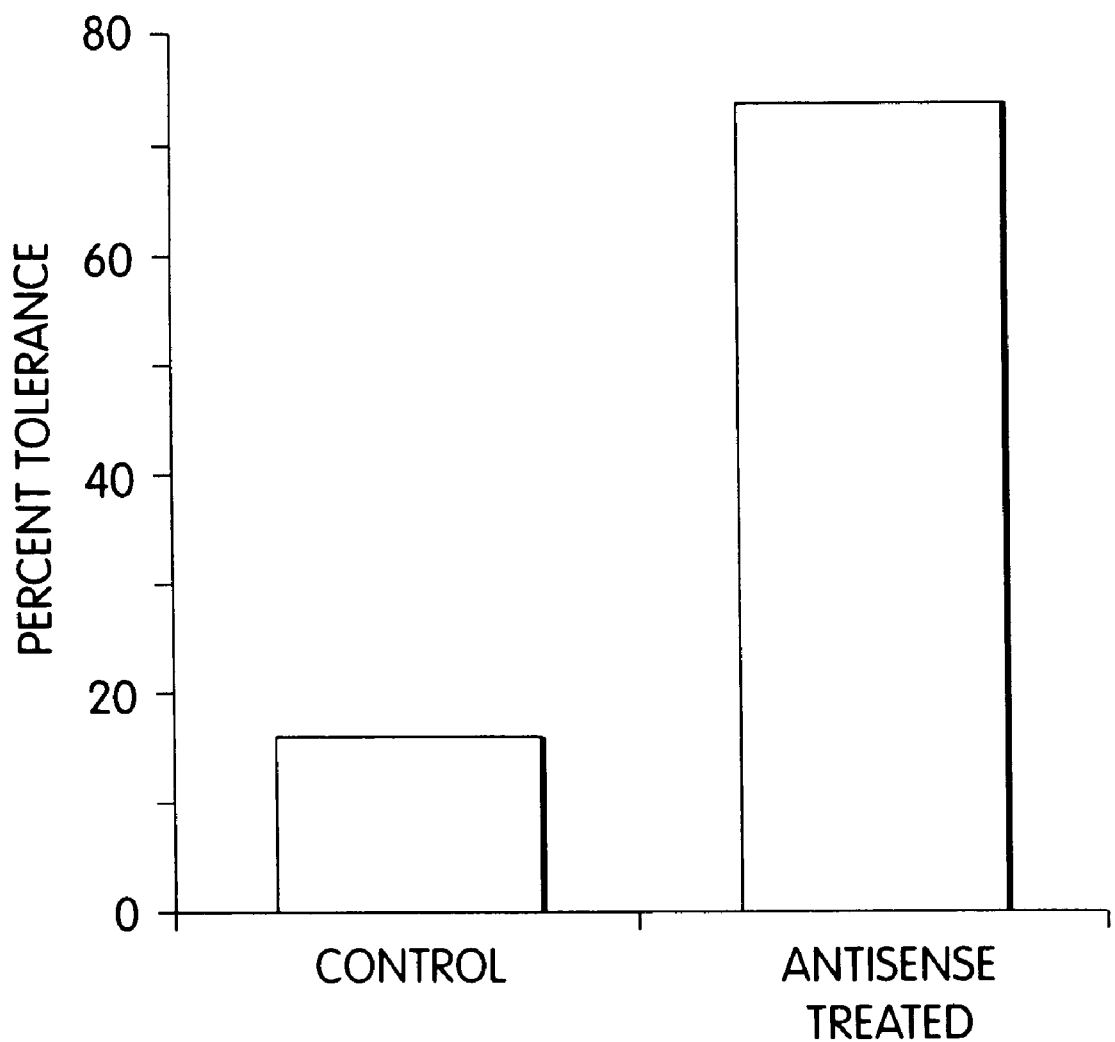

FIG. 13-A shows transfection efficiencies for rat hearts transfected ex vivo with FITC-ODN, with and without pressure. A FITC-ODN solution (80 µM) was perfused into the coronary arteries of donor hearts after aortic crossclamping. The hearts were submerged in FITC-ODN solution and exposed to either 0 atm or 2 atm above ambient pressure for 45 minutes at 4° C., as shown in FIG. 6. The hearts were then heterotopically transplanted into the abdominal aorta and vena cava of recipient rats. Nuclear localization of FITC was assessed 24 hours after transplantation by fluorescent microscopy of sections co-stained with a fluorescent DNA-intercalating dye. Transfection efficiency is expressed as cells displaying nuclear localization of FITC-ODN as a percent of total cells. n=3, p<0.005.

FIG. 13-B shows ICAM-1 expression in transplanted rat hearts with and without pressure-mediated transfection of antisense-ICAM-1 ODN. Either saline (control) or antisense-ICAM-1-ODN solution (80 µM) was perfused into the coronary arteries of donor PVG strain hearts after aortic crossclamping. The hearts were then submerged in FITC-ODN solution and exposed to 2 atm above ambient pressure for 45 minutes at 4° C., as illustrated in FIG. 6. Tissue was harvested 3 days after heterotopic transplantation into ACI recipients. ICAM-1 positive area was measured by image analysis of sections stained immunohistochemically for ICAM-1. n=3–6, p=0.04.

FIG. 13-C illustrates the induction of long-term graft acceptance by pressure-mediated transfection of transplanted rat hearts with antisense ODN against ICAM-1. PVG strain rat hearts were harvested and transfected ex-vivo with either antisense-ICAM-1 ODN solution (80 µm) or with saline solution (control), as described above in relation to FIG. 13-B. The hearts were then heterotopically transplanted into ACI strain recipients. All animals were systemically administered anti-LFA-1 antibody for 6 days following transplantation, to block the ligand for ICAM-1. No further immunosupression was administered. Tolerance is reported as percentage of treated animals found to have long term acceptance of their allografts. Graft acceptance was defined by presence of heart beat in the graft for >100 days. Control n=12, antisense-treated n=27, p=0.003.

EXAMPLE 8

Figure 14A:
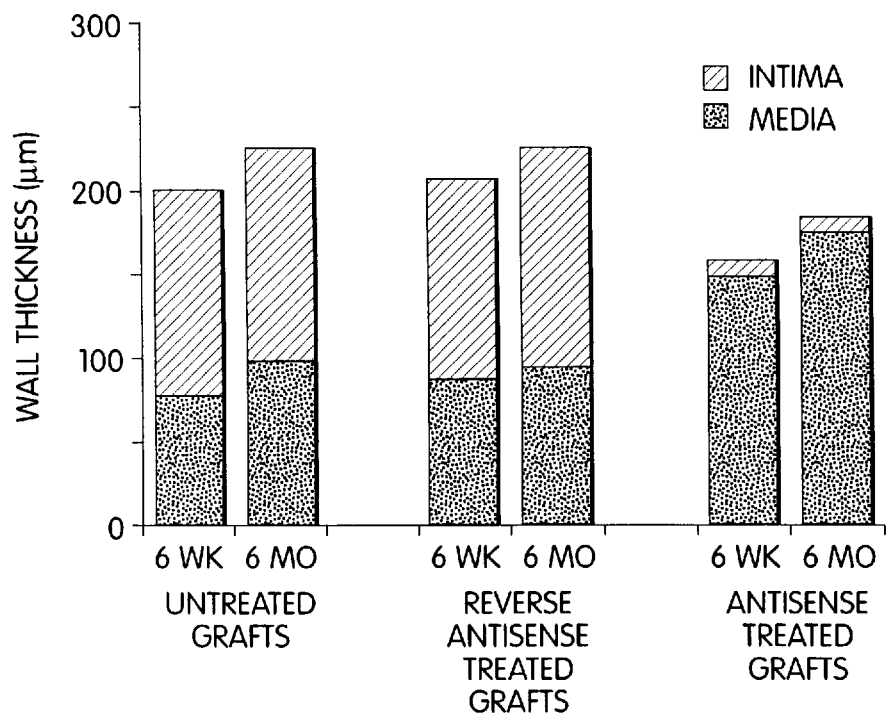
FIG. 14-A shows wall thicknesses at 6 weeks and 6 months after transplantation for untreated (control) grafts, and grafts transfected with either reverse antisense (control) ODN or with antisense ODN against both PCNA and cdc2 kinase, according to the present invention.
Figure 14B:
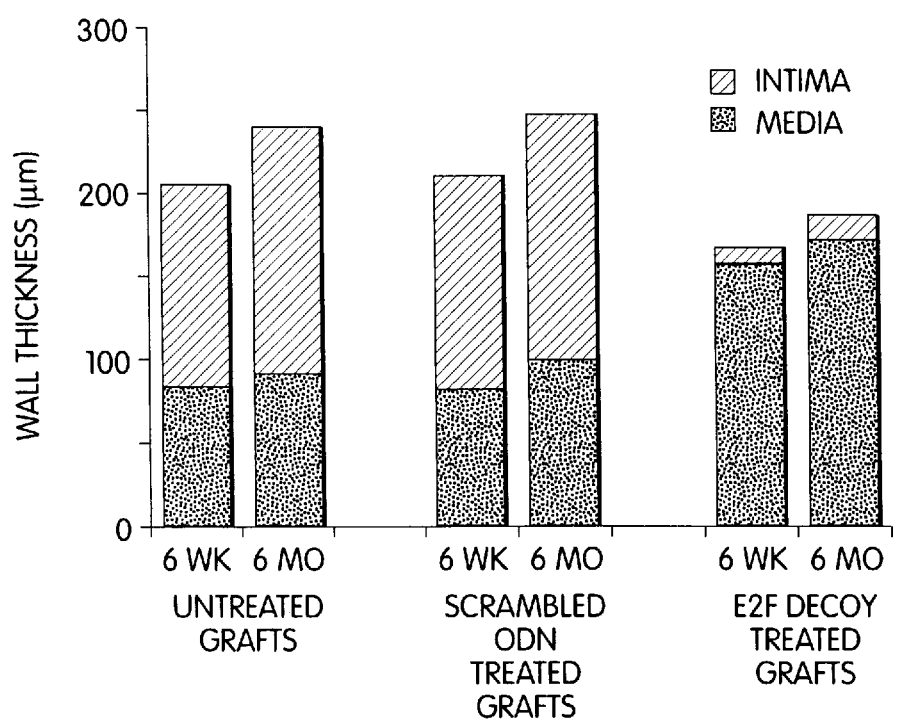

FIGS. 14-A and 14-B show inhibition of neointimal hyperplasia in rabbit jugular veins grafted into carotid arteries, following pressure-mediated transfection with ODN designed to block upregulation of cell cycle regulatory genes.

FIG. 14-A shows wall thicknesses at 6 weeks and 6 months after transplantation for untreated (control) grafts, and grafts transfected with either reverse antisense (control) ODN or with antisense ODN against both PCNA and cdc2 kinase. Neointima formation was inhibited for up to 6 months, while medial hypertrophy allows adaptive wall thickening to reduce wall stress in the high-pressure arterial environment. FIG. 14-B shows results similar to those in FIG. 14-A for veins transfected with E2F decoy ODN, as compared to untreated grafts and control grafts transfected with scrambled ODN. n=6, p<0.005.

Although the above descriptions contain many specificities, these should not be construed as limitations on the scope of the invention, but rather as illustrations of particular embodiments thereof. For example, a time-varying incubation pressure can be used in general. Many potential designs for enclosing means, protective means, and/or occluding means can be readily devised by the skilled artisan, depending on the application. Various incubation pressures, periods, and active agent dosages leading to near-maximal transfection efficiencies can be readily determined for different tissue types.

In general, any composition containing a nucleic acid can be used with a method of the present invention. Examples of such compositions are solutions comprising DNA or RNA oligonucleotides, polynucleotides, plasmids, aptomers, modified forms of DNA or RNA (e.g. phosphorothioates or ribozymes), or proteins bound to DNA. Clearly, the sequence of the delivered nucleic acid depends on the application.

Accordingly, the scope of the invention should be determined not by the embodiments illustrated, but by the appended claims and their legal equivalents.

What is claimed is:

1. A method of delivering a nucleic acid into a cell, said method comprising the steps of:
    a) placing said nucleic acid in an extracellular environment of said cell;
    b) defining an enclosure comprising said cell and said extracellular environment; and
    c) establishing an incubation pressure within said enclosure whereby an establishment of said incubation pressure facilitates an uptake of said nucleic acid by said cell.

2. The method of claim 1 wherein a boundary of said enclosure is defined substantially by an enclosing means.

3. The method of claim 2 wherein said enclosing means comprises a pressurization chamber.

4. The method of claim 1 wherein part of a boundary of said enclosure is defined by a tissue.

5. The method of claim 4 further comprising the step of establishing a protective means adapted to be placed around said tissue, for preventing a trauma in said tissue.

6. The method of claim 4 further comprising the steps of:
    a) establishing a first occlusion in a first organ conduit in communication with an organ; and
    b) establishing a second occlusion in a second organ conduit in communication with said organ;
    wherein said substantial part of said boundary is defined by a tissue of said organ.

7. The method of claim 1 comprising the step of establishing said incubation pressure within an entire organ, said organ comprising said cell.

8. The method of claim 7 wherein said organ is a heart.

9. The method of claim 1 comprising the step of establishing said incubation pressure around an organism, said organism comprising said cell.

10. The method of claim 9 comprising the step of perfusing said nucleotide into a target region of said organism.

11. The method of claim 1 comprising maintaining said incubation pressure at a predetermined level.

12. The method of claim 1 wherein said incubation pressure is between 0 atm and 2 atm above atmospheric pressure.

13. The method of claim 1 wherein said incubation pressure is between 300 mm Hg and 1500 mm Hg above atmospheric pressure.

14. The method of claim 1 wherein said incubation pressure is higher than 100 mm Hg.

15. The method of claim 1 comprising maintaining said incubation pressure for a predetermined incubation period.

16. The method of claim 1 comprising maintaining said incubation pressure for an incubation period longer than 1 minute.

17. The method of claim 1 comprising maintaining said incubation pressure for an incubation period longer than 1 hour.

18. The method of claim 1 wherein:
 a) said cell is a mammalian cell in a tissue; and
 b) said method comprises establishing said incubation pressure around said tissue.

19. The method of claim 18 wherein said tissue comprises a part of an organ selected from the group consisting of the liver, kidneys, and bone marrow.

20. The method of claim 18 wherein said tissue comprises a part of an organ selected from the group consisting of bones, muscles, connective tissue, gastrointestinal organs, endocrine organs, and exocrine organs.

21. The method of claim 18 wherein said tissue comprises a part of a heart.

22. The method of claim 18 wherein said tissue comprises a part of a blood vessel.

23. The method of claim 22 wherein said tissue comprises a part of a vein.

24. The method of claim 1 wherein said nucleic acid is naked.

25. The method of claim 1 wherein said nucleic acid is attached to a liposome.

26. The method of claim 1 wherein said nucleic acid is attached to a viral vector.

27. The method of claim 1 wherein said nucleic acid is attached to a virus-liposome complex.

28. The method of claim 27 wherein said nucleic acid is attached to a hemagglutinating virus of Japan-liposome complex.

29. The method of claim 1 wherein said nucleic acid is attached to a molecule of interest.

30. The method of claim 29 wherein said molecule of interest comprises a protein.

31. The method of claim 1 wherein said nucleic acid comprises a deoxyribonucleic acid.

32. The method of claim 1 wherein said nucleic acid comprises a ribonucleic acid.

33. The method of claim 1 wherein:
 a) said nucleic acid comprises a decoy double stranded deoxyribonucleic acid having a binding site; and
 b) a cellular factor present in said cell is adapted to bind to said binding site;
 whereby said cellular factor binds to said binding site.

34. The method of claim 1 wherein said nucleic acid comprises a plasmid.

35. The method of claim 1 wherein said nucleic acid comprises a regulatory element operatively linked to a coding portion.

36. The method of claim 35 wherein said regulatory element is selected from the group consisting of promoters and enhancers.

37. The method of claim 1 wherein said nucleic acid encodes a protein adapted to be secreted by said cell.

38. The method of claim 1 comprising the step of establishing in vitro said incubation pressure around a cell culture comprising said cell.

39. A system for delivering a nucleic acid into a cell, said system comprising:
 a) an enclosing means for defining at least part of a boundary of an enclosure, said enclosure containing said cell and an extracellular enviroment of said cell, said extracellular enviroment containing said nucleic acid; and
 b) a pressurization means for establishing an incubation pressure within said enclosure;
 whereby an establishment of said incubation pressure facilitates an uptake of said nucleic acid by said cell.

40. The system of claim 39 further comprising a delivery means for delivering said nucleic acid to said extracellular environment.

41. The system of claim 39 wherein said enclosing means comprises an impermeable sheath.

42. The system of claim 39 wherein said enclosing means comprises an occlusion means for occluding a passage in a tissue.

43. The system of claim 39 wherein said enclosing means comprises a pressurization chamber.

44. The system of claim 39 wherein said boundary is defined substantially by said enclosing means.

45. The system of claim 39 wherein part of said boundary is defined by a tissue.

46. The system of claim 45 further comprising a protective means adapted to be placed around said tissue, for preventing a trauma in said tissue.

47. The system of claim 46 wherein said protective means comprises an inelastic sheath.

48. A method of delivering a molecule into a cell, said method comprising the steps of:
 a) placing said molecule in an extracellular environment of said cell comprising a liquid medium; and
 b) non-surgical establishing enclosure around said cell and said liquid medium and establishing an incubation pressure around said cell and said extracellular environment;
 wherein said molecule is selected from the group consisting of a drug, sugar, fatty acid and protein and whereby an establishment of said incubation pressure facilitates an uptake of said molecule by said cell.

49. The method of claim 48 wherein said molecule comprises a sugar.

50. The method of claim 48 wherein said molecule comprises a fatty acid.

51. The method of claim 48 wherein said molecule comprises a protein.

52. The method of claim 48 wherein said molecule comprises a drug.

53. The method of claim 48, wherein said cell is in a living mammal.

54. The method of claim 48, wherein part of a boundary of said enclosure is defined by a tissue.

55. The method of claim 54 further comprising the steps of:
 a) establishing a first occlusion on a first organ conduit in communication with an organ; and
 b) establishing a second occlusion in a second organ conduit in communication with said organ;
 wherein said substantial part of said boundary is defined by tissue of said organ.

56. The method of claim 55 wherein said organ is a heart.

57. The method of claim 48 comprising the step of establishing said incubation pressure around an organism that comprises said cell.

58. The method of claim 57 comprising the step of perfusing said molecule into a target region of said organism.

59. The method of claim 48 comprising maintaining said incubation pressure for a predetermined incubation period.

60. The method of claim 59 comprising maintaining said incubation pressure for an incubation period longer than 1 minute.

61. The method of claim 60 comprising maintaining said incubation pressure for an incubation period longer than 1 hour.

62. The method of claim 48 wherein said cell is in a tissue that comprises a part of an organ selected from the group consisting of bones, muscles, connective tissue, gastrointestinal organs, endocrine organs, and exocrine organs.

63. The method of claim 48 wherein said cell is in a tissue that comprises a part of an organ selected from the group consisting of the liver, kidneys, and bone marrow.

64. The method of claim 48 wherein said tissue comprises a part of a heart.

65. The method of claim 48 wherein said tissue comprises a part of a blood vessel.

66. The method of claim 65 wherein said tissue comprises a part of a vein.

67. The method of claim 48 wherein said molecule is attached to a liposome.

68. The method of claim 48 wherein said uptake reduces an immune response of a patient to said cell.

69. The method of claim 48 wherein said cell is an organ and said incubation pressure is established within the entire organ.

70. A method of delivering a molecule into a cell, said method comprising the steps of:
   a) placing said molecule in an extracellular environment of said cell comprising a liquid medium; and
   b) establishing an enclosure around said cell and said liquid medium and establishing an incubation pressure around said cell and said extracellular environment using external pressurizing means;
wherein said molecule is selected from the group consisting of a drug, sugar, fatty acid and protein and whereby an establishment of said incubation pressure facilitates uptake of said molecule by said cell.

71. The method of claim 70 wherein a boundary of said enclosure is defined substantially by an enclosing means.

72. The method of claim 71 wherein said enclosing means comprises a pressurization chamber.

73. The method of claim 70 further comprising the step of establishing a protective means adapted to be placed around said tissue for preventing a trauma in said tissue.

74. The method of claim 70, further comprising maintaining said incubation pressure at a predetermined level.

75. The method of claim 74 wherein said incubation pressure is between 0 atm and 2 atm above atmospheric pressure.

76. The method of claim 74 wherein said incubation pressure is between 300 mm Hg and 1500 mm Hg above atmospheric pressure.

77. The method of claim 74 wherein said incubation pressure is higher than 100 mm Hg.

78. The method of claim 70, wherein said incubation pressure is established in vitro around a cell culture comprising said cell.

79. The method of claim 70, wherein said external pressurizing means comprises a sheath.

80. The method of claim 70, wherein said external pressurizing means does not cause continuous flow through the vasculature supplying said cell.

81. The method of claim 80, wherein said cell is in a living mammal.

82. The method of claim 80, further comprising the step of establishing said incubation pressure within an organ that comprises said cell.

83. The method of claim 80, wherein said method is carried out ex vivo.

84. The method of claim 80, wherein:
   a) said cell is a mammalian cell in a tissue; and
   b) said method further comprises establishing said incubation pressure by applying pressure to the outer surface of said tissue.

85. The method of claim 70, wherein said molecule is delivered to the cavity of a hollow internal organ.

86. A system for delivering a molecule into a cell, said system comprising:
   a) enclosing means for non-surgically defining at least part of a boundary of an enclosure, said enclosure containing said cell and an extracelllular enviroment of said cell that contains said molecule; and
   b) a pressurization means for establishing an incubation pressure within said enclosure;
   wherein said molecule is selected from the group consisting of a drug, sugar, fatty acid and protein and whereby an establishment of said incubation pressure facilitates the uptake of said molecule by said cell.

87. The system of claim 86, further comprising a delivery means for delivering said molecule to said extracellular environment.

88. The system of claim 86, wherein said enclosing means comprises a pressurization chamber.

89. The system of claim 86, wherein said boundary is defined substantially by said enclosing means.

90. The system of claim 86, wherein said enclosing means defines the entire boundary of said sealed enclosure.

* * * * *